United States Patent
Koh

(10) Patent No.: US 10,969,398 B2
(45) Date of Patent: Apr. 6, 2021

(54) DETECTION OF METABOLITES FOR CONTROLLED SUBSTANCES

(71) Applicant: National Technology & Engineering Solutions of Sandia, LLC, Albuquerque, NM (US)

(72) Inventor: Chung-Yan Koh, Dublin, CA (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 17 days.

(21) Appl. No.: 16/282,050

(22) Filed: Feb. 21, 2019

(65) Prior Publication Data

US 2019/0187163 A1 Jun. 20, 2019

Related U.S. Application Data

(62) Division of application No. 14/957,405, filed on Dec. 2, 2015, now Pat. No. 10,254,298.

(Continued)

(51) Int. Cl.
*G01N 33/94* (2006.01)
*G01N 21/64* (2006.01)
*B01L 3/00* (2006.01)

(52) U.S. Cl.
CPC ............ *G01N 33/948* (2013.01); *B01L 3/502* (2013.01); *G01N 21/6428* (2013.01);
(Continued)

(58) Field of Classification Search
None
See application file for complete search history.

(56) References Cited

U.S. PATENT DOCUMENTS

| 3,555,284 A | 1/1971 | Anderson |
| 3,744,974 A | 7/1973 | Maddox |

(Continued)

FOREIGN PATENT DOCUMENTS

| WO | WO-2008/143578 | 11/2008 |
| WO | WO-2009/098237 | 8/2009 |

OTHER PUBLICATIONS

U.S. Appl. No. 14/957,405, filed Dec. 2, 2015, Koh.
(Continued)

*Primary Examiner* — Rebecca M Giere
(74) *Attorney, Agent, or Firm* — Medley, Behrens & Lewis, LLC

(57) ABSTRACT

The various technologies presented herein relate to identifying whether an individual has taken, and/or is under the influence of, a restricted drug. A density separation technique is utilized, wherein a sample (e.g., blood, saliva, urine, etc.) which may include an analyte is exposed to a first plurality of beads having an analyte attached thereto, a second plurality of beads having a metabolite-specific antibody attached thereto, and a plurality of fluorophore-labelled analyte-specific antibodies. After incubation, any analyte in the sample (e.g., delta-9-THC) is bound to the fluorophore-labelled analyte-specific antibodies, any free fluorophore-labelled analyte-specific antibodies are attached to the analyte of the first beads, and any metabolite in the sample is bound to the second antibody. By applying centrifugal separation, the first beads move to a region which undergoes irradiation. If no fluorescence occurs, the sample includes the analyte; if fluorescence occurs, the sample does not include the analyte.

14 Claims, 12 Drawing Sheets

Related U.S. Application Data

(60) Provisional application No. 62/138,040, filed on Mar. 25, 2015.

(52) U.S. Cl.
CPC .................. *B01L 2200/0647* (2013.01); *B01L 2300/0861* (2013.01); *B01L 2400/0409* (2013.01); *G01N 2021/6439* (2013.01)

(56) References Cited

U.S. PATENT DOCUMENTS

| | | | |
|---|---|---|---|
| 4,125,375 | A | 11/1978 | Hunter |
| 4,156,570 | A | 5/1979 | Wardlaw |
| 4,554,071 | A | 11/1985 | Ruijten et al. |
| 4,656,143 | A | 4/1987 | Baker et al. |
| 4,683,579 | A | 7/1987 | Wardlaw |
| 4,833,073 | A | 5/1989 | McNally |
| 4,844,818 | A | 7/1989 | Smith |
| 5,279,936 | A | 1/1994 | Vorpahl |
| 5,635,362 | A | 6/1997 | Levine et al. |
| 5,639,428 | A | 6/1997 | Cottingham |
| 5,705,628 | A | 1/1998 | Hawkins |
| 5,882,903 | A | 3/1999 | Andrevski et al. |
| 5,892,577 | A | 4/1999 | Gordon |
| 6,153,148 | A | 11/2000 | Thomas |
| 6,319,469 | B1 | 11/2001 | Mian et al. |
| 6,503,722 | B1 | 1/2003 | Valkirs |
| 6,887,384 | B1 | 5/2005 | Frechet et al. |
| 6,960,449 | B2 | 11/2005 | Wang et al. |
| 7,033,747 | B2 | 4/2006 | Gordon et al. |
| 7,157,049 | B2 | 1/2007 | Valencia et al. |
| 7,312,085 | B2 | 12/2007 | Chou et al. |
| 7,332,326 | B1 | 2/2008 | Kellogg et al. |
| 7,749,772 | B1 | 7/2010 | Wang |
| 7,758,810 | B2 | 7/2010 | Lee et al. |
| 7,790,400 | B2 | 9/2010 | Jehanli et al. |
| 8,337,775 | B2 | 12/2012 | Pugia et al. |
| 8,945,914 | B1 | 2/2015 | Schaff et al. |
| 8,962,346 | B2 | 2/2015 | Schaff et al. |
| 9,186,668 | B1 | 11/2015 | Schaff et al. |
| 9,244,065 | B1 | 1/2016 | Schaff et al. |
| 9,304,128 | B1 | 4/2016 | Koh et al. |
| 9,304,129 | B2 | 4/2016 | Schaff et al. |
| 9,500,579 | B1 | 11/2016 | Sommer et al. |
| 9,702,871 | B1 | 7/2017 | Koh et al. |
| 9,766,230 | B1 | 9/2017 | Koh et al. |
| 9,795,961 | B1 | 10/2017 | Koh et al. |
| 9,803,238 | B1 | 10/2017 | Koh et al. |
| 9,903,001 | B1 | 2/2018 | Koh et al. |
| 10,024,849 | B2 | 7/2018 | Schaff et al. |
| 2001/0055812 | A1 | 12/2001 | Mian et al. |
| 2002/0098535 | A1 | 7/2002 | Wang et al. |
| 2002/0106786 | A1 | 8/2002 | Carvalho et al. |
| 2002/0137068 | A1 | 9/2002 | Haugland et al. |
| 2002/0151043 | A1 | 10/2002 | Gordon |
| 2002/0153251 | A1 | 10/2002 | Sassi et al. |
| 2002/0164659 | A1 | 11/2002 | Rao et al. |
| 2002/0170825 | A1 | 11/2002 | Lee et al. |
| 2003/0013203 | A1 | 1/2003 | Jedrzejewski et al. |
| 2003/0124719 | A1 | 7/2003 | Woodside |
| 2003/0203504 | A1 | 10/2003 | Hefti |
| 2004/0072278 | A1 | 4/2004 | Chou et al. |
| 2005/0186685 | A1 | 8/2005 | Kange et al. |
| 2005/0191682 | A1 | 9/2005 | Barone et al. |
| 2005/0215410 | A1 | 9/2005 | Merino et al. |
| 2005/0282220 | A1 | 12/2005 | Prober et al. |
| 2006/0078955 | A1 | 4/2006 | Lin et al. |
| 2006/0171654 | A1 | 8/2006 | Hawkins et al. |
| 2008/0053194 | A1 | 3/2008 | Ahmad |
| 2008/0108047 | A1 | 5/2008 | Woodside |
| 2008/0149484 | A1 | 6/2008 | Tolley et al. |
| 2009/0004059 | A1 | 1/2009 | Pugia et al. |
| 2009/0069554 | A1 | 3/2009 | Finne |
| 2009/0209402 | A1 | 8/2009 | Andersson |
| 2009/0325186 | A1 | 12/2009 | Hinnah et al. |
| 2010/0068754 | A1 | 3/2010 | Kirakossian |
| 2010/0120596 | A1 | 5/2010 | Froman et al. |
| 2010/0151560 | A1 | 6/2010 | Wo et al. |
| 2011/0045958 | A1 | 2/2011 | Pedrazzini |
| 2013/0260447 | A1 | 10/2013 | Link |
| 2014/0273241 | A1 | 9/2014 | Ochranek et al. |
| 2015/0360225 | A1 | 12/2015 | Schaff et al. |
| 2016/0061829 | A1 | 3/2016 | Schaff et al. |
| 2016/0178619 | A1 | 6/2016 | Koh et al. |
| 2018/0037932 | A1 | 2/2018 | Koh et al. |
| 2018/0037960 | A1 | 2/2018 | Koh et al. |
| 2018/0065118 | A1 | 3/2018 | Koh et al. |

OTHER PUBLICATIONS

U.S. Appl. No. 15/785,708, filed Oct. 17, 2017, Koh et al.
U.S. Appl. No. 15/669,426, filed Aug. 4, 2017, Phaneuf et al.
Abi-Samra et al., "Infrared controlled waxes for liquid handling and storage on a CD-microfluidic platform", Lab on a Chip, 2011, vol. 11, pp. 723-726.
Ahanotu et al., "Staphylococcal enterotoxin B as a biological weapon: recognition, management, and surveillance of Staphylococcal enterotoxin", Applied Biosafety, 2006, vol. 11 (3), pp. 120-126.
Albrecht et al., "Micro free-flow IEF enhanced active cooling and functionalized gels", Electrophoresis, 2006, vol. 27, pp. 4960-4969.
Amersham Biosciences AB, "Percoll: Methodology and Applications", Handbook No. 18-1115-69 (Ed. AC), 2001, Uppsala, Sweden, pp. 1-84.
Amukele et al., "Ricin A-chain activity on stem-loop and unstructured DNA substrates", Biochemistry, 2005, vol. 44(11), pp. 4416-4425.
Andersson et al., "Parallel nanoliter microfluidic analysis system", Analytical Chemistry, 2007, vol. 79(11), pp. 4022-4030.
Baldwin, "How Hofmeister ion interactions affect protein stability", Biophysical Journal, 1996, vol. 71, pp. 2056-2063.
Berlier et al., "Quantitative comparison of long-wavelength Alexa Fluor dyes to Cy dyes: fluorescence of the dyes and their bioconjugates", Journal of Histochemistry and Cytochemistry, 2003, vol. 51(12), pp. 1699-1712.
Berry et al., "One-step purification of nucleic acid for gene expression analysis via immiscible filtration assisted by surface tension", Lab on a Chip, 2011, vol. 11(10), pp. 1747-1753.
Boyko et al., "Cell-free DNA—a marker to predict ischemic brain damage in a rat stroke experimental model", Journal of Neurosurgery and Anesthesiology, 2011, vol. 23(3), pp. 222-228.
Brigotti et al., "Shiga toxin 1 acting on DNA in vitro is a heat-stable enzyme not requiring proteolytic activation", Biochimie Journal, 2004, vol. 86(45), pp. 305-309.
Buck et al., "Design strategies and performance of custom DNA sequencing primers", Biotechniques, 1999, vol. 27(3), pp. 528-536.
Carbera et al., "Formation of natural pH gradients in a microfluidic device under flow conditions: model and experimental validation", Analytical Chemistry, 2001, vol. 73(3), pp. 658-666.
Carney, "Rapid diagnostic tests employing latex particles", Analytical Proceedings, 1990, vol. 27, pp. 99-100.
Carter et al., "Rapid detection of a specific trimethoprim resistance gene using a biotinylated DNA probe", Journal of Antimicrobial Chemotherapy, 1987, vol. 20(3), pp. 335-341.
Cary, "The marijuana detection window: determining the length of time cannabinoids will remain detectable in urine following smoking", National Drug Court Institute, 2006, vol. IV(2), pp. 1-16.
Churchill et al., "Detection of Listeria monocytogenes and the toxin listeriolysin O in food", Journal of Microbiological Methods, 2006, vol. 64(2), pp. 141-170.
Cui et al., "Multistage isoelectric focusing in a polymeric microfluidic chip", Analytical Chemistry, 2005, vol. 77(24), pp. 7878-7886.
Curtis et al., "A molecular approach to bioseparations: protein-protein and protein-salt interactions", Chemical Engineering Science, 2006, vol. 61, pp. 907-923.

(56) References Cited

OTHER PUBLICATIONS

Czeiger et al., "Measurement of circulating cell-free DNA levels by a new simple fluorescent test in patients with primary colorectal cancer", American Journal of Clinical Pathology, 2011, vol. 135(2), pp. 264-270.
Das et al., "Effects of separation length and voltage on isoelectric focusing in a plastic microfluidic device", Electrophoresis, 2006, vol. 27(18), pp. 3619-3626.
Endo et al., "RNA N-glycosidase activity of ricin A-chain. Mechanism of action of the toxic lectin ricin on eukaryotic ribosomes", The Journal of Biological Chemistry, 1987, vol. 262(17), pp. 8128-8130.
Fologea et al, "Detecting single stranded DNA with a solid state nanopore", Nano Letters, 2005, vol. 5(10), pp. 1905-1909.
Glorikian et al., "Microfluidics for IVDS—Smart consumable product development: implications for molecular diagnostics", DX Directions, 2010, Spring, pp. 12-16.
Goldshtein et al., "A rapid direct fluorescent assay for cell-free DNA quantification in biological fluids", Annals of Clinical Biochemistry, 2009, vol. 46(Pt 6), pp. 488-494.
Gorkin et al., "Centrifugal microfluidics for biomedical applications", Lab on a Chip, 2010, vol. 10, pp. 1758-1773.
Gusev et al., "Capillary columns with in situ formed porous monolithic packing for micro high-performance liquid chromatography and capillary electrochromatography", Journal of Chromatography A, 1999, vol. 855(1), pp. 273-290.
Hatch et al., "Integrated preconcentration SDS-PAGE of proteins in microchips using photopatterned cross-linked polyacrylamide gels", Analytical Chemistry, 2006, vol. 78(14), pp. 4976-4984.
Herr et al., "Microfluidic immunoassays as rapid saliva-based clinical diagnostics", Proceedings of the National Academy of Science USA, 2007, vol. 104(13), pp. 5268-5273.
Herr et al., "On-chip coupling of isoelectric focusing and free solution electrophoresis for multidimensional separations", Analytical Chemistry, 2003, vol. 75(5), pp. 1180-1187.
Holmberg et al., "Depurination of A4256 in 28 S rRNA by the ribosome-inactivating proteins from barley and ricin results in different ribosome conformations", Journal of Molecular Biology, 1996, vol. 259(1), pp. 81-94.
Holmes et al., "Leukocyte analysis and differentiation using high speed microfluidic single cell impedance cytometry", Lab on a Chip, 2009, vol. 9, pp. 2881-2889.
Huang et al., "The primary structure of Staphylococcal enterotoxin B: III. The cyanogen bromide peptides of reduced and aminoethylated enterotoxin B, and the complete amino acid sequence", Journal of Biological Chemistry, 1970, vol. 245(14), pp. 3518-3525.
Huang et al., "Microfabrication of a tapered channel for isoelectric focusing with thermally generated pH gradient," Electrophoresis, 2002, vol. 23(20), pp. 3504-3510.
IVD Technology, "Microfluidic applications for IVDs", DX Directions, 2010, Spring, pp. 1-26.
Kim et al., "Fully integrated lab-on-a-disc for nucleic acid analysis of food-borne pathogens", Analytical Chemistry, 2014, vol. 86, pp. 3841-3848.
Koh et al., "Centrifugal microfluidic platform for ultrasensitive detection of botulinum toxin", Analytical Chemistry, 2015, vol. 81, pp. 922-928.
Lauridsen et al., "Nucleic aptamers against biotoxins: a new paradigm toward the treatment and diagnostic approach", Nucleic Acid Therapeutics, 2012, vol. 22, pp. 371-379.
Lee et al., "Fully integrated lab-on-a-disc for simultaneous analysis of biochemistry and immunoassay from whole blood", Lab on a Chip, 2011, vol. 11(1), pp. 70-78.
Lee et al., "A fully automated immunoassay from whole blood on a disc", Lab on a Chip, 2009, vol. 9(11), pp. 1548-1555.
Lim et al., "Bead-based microfluidic immunoassays: Tthe next generation", Biosensors and Bioelectronics, 2007, vol. 22(7), pp. 1197-1204.
Lim et al., "Rapid isoelectric trapping in a micropreparative-scale multicompartment electrolyzer", Electrophoresis, 2007, vol. 28(12), pp. 1851-1859.
Lo et al., "Photopolymerized diffusion-defined polyacrylamide gradient gels for on-chip protein sizing", Lab on a Chip, 2008, vol. 8(8), pp. 1273-1279.
Lo et al., "Plasma DNA as a prognostic marker in trauma patients", Clinical Chemistry, 2000, vol. 46(3), pp. 319-323.
Long et al., "Integration of nanoporous membranes for sample filtration/preconcentration in microchip electrophoresis", Electrophoresis, 2006, vol. 27(24), pp. 4927-4934.
Madou et al., "Lab on a CD", Annual Review of Biomedical Engineering, 2006, vol. 8, pp. 601-628.
Maes et al., "Comparison of sample fixation and the use of LDS-751 or anti-CD45 or leukocyte identification in mouse whole blood for flow cytometry", Journal of Immunological Methods, 2007, vol. 319(1-2), pp. 79-86.
McBain et al., "Polyethyleneimine functionalized iron oxide nanoparticles as agents for DNA delivery and transfection", Journal of Material Chemistry, 2007, vol. 17(24), pp. 2561-2565.
Melting Temperature Calculation. Retrieved on asf from the internet: http://www.biophp.org/minitools/melting_temperature/demo.php?primer=CGT+TAC+CCG+CAG&basic-1&NearestNeighbor=1&cp=200&cs=50&cmg=0.
Min et al., "Functional integration of DNA purification and concentration into a real time micro-PCR chip", Lab on a Chip, 2011, vol. 11(2), pp. 259-265.
Niedbala et al., "Detection of marijuana use by oral fluid and urine analysis following single-dose administration of smoked and oral marijuana", Journal of Analytical Toxicology, 2001, vol. 25, pp. 289-303.
Price et al., "Light-scattering immunoassay", in Principles and Practice Immunoassay (Second Ed., C.P. Price & D.J. Newman, eds.), 1997, Stockton Press (New York, NY), Chap. 18, pp. 445-480.
PubChem Search results for "2,3-dihydroxypropyl octanoate," retrieved on Oct. 5, 2016 from https://www.ncbi.nlm.nih.gov/pcompound/?term=2%2C3-dihydroxypropyl+octanoate (4 pp.).
PubChem Entry for "TWEEN 20," retrieved on Oct. 4, 2016 from https://pubchem.ncbi.nlm.nih.gov/compound/Tween_20#section=Names-and-identifiers (2 pp.).
Rhodes et al., "Plasma DNA concentration as a predictor of mortality and sepsis in critically ill patients", Critical Care, 2006, vol. 10(2), Article R60 (pp. 1-7).
Riahi et al., "Molecular detection of bacterial pathogens using microparticle enhanced double-stranded DNA probes", Analytical Chemistry, 2011, vol. 83(16), pp. 6349-6354 and Supporting Information (8 pp.).
Rider et al., "A B cell-based sensor for rapid identification of pathogens", Science, 2003, vol. 301, pp. 213-215.
Riegger et al., "Read-out concepts for multiplexed bead-based fluorescence immunoassays on centrifugal microfluidic platforms", Sensors and Actuators A—Physical, 2006, vol. 126, pp. 455-462.
Saukkonen et al., "Cell-free plasma DNA as a predictor of outcome in severe sepsis and septic shock", Clinical Chemistry, 2008, vol. 54(6), pp. 1000-1007.
Schaff et al., "Whole blood immunoassay based on centrifugal bead sedimentation", Clinical Chemistry, 2011, vol. 57(5), pp. 753-761.
Schembri et al., "Portable simultaneous multiple analyte whole-blood analyzer for point-of-care testing", Clinical Chemistry, 1992, vol. 38(9), pp. 1665-1670.
Schneider et al., "Characterization of EBV-genome negative "null" and "t" cell lines derived from children with acute lymphoblastic leukemia and leukemic transformed non-Hodgkin lymphoma", International Journal of Cancer, 1977, vol. 19(5), pp. 621-626.
Sigma-Aldrich product page for TWEEN 20, archived from Jun. 28, 2012, retrieved on Oct. 5, 2016 from https://web.archive.org/web/20120628080753/http://www.sigmaaldrich.com/catalog.product/sial/p1379?ang=en&region= (43 pp.).
Sommer et al., "On-chip isoelectric focusing using photopolymerized immobilized pH gradients", Analytical Chemistry, 2008, vol. 80(9), pp. 3327-3333.

(56) References Cited

OTHER PUBLICATIONS

Suzuki et al., "Experimental optimization of probe length to increase the sequence specificity of high-density oligonucleotide microarrays", BMC Genomics, 2007, vol. 8, Art. 373 (13 pp.).

Tan et al., "Miniaturized capillary isoelectric focusing in plastic microfluidic devices", Electrophoresis, 2002, vol. 23(20), pp. 3638-3645.

Yu et al., "Bioinformatic processing to identify single nucleotide polymorphism that potentially affect Ape1 function", Mutation Research/Genetic Toxicology and Environmental Mutagenesis, 2011, vol. 722(2), pp. 140-146.

Zhang et al., "A new biodosimetric method: branched DNA-based quantitative detection of B1 DNA in mouse plasma", British Journal of Radiology, 2010, vol. 83, pp. 694-701.

Ziegler et al., "Circulating DNA: a new diagnostic gold mine?", Cancer Treatment Reviews, 2002, vol. 28, pp. 255-271.

Zilberstein et al., "Parallel isoelectric focusing chip", Proteomics, 2004, vol. 4(9), pp. 2533-2540.

Zilberstein et al., "Parallel isoelectric focusing II", Electrophoresis, 2004, vol. 25(21-22), pp. 3643-3651.

Zilberstein et al., "Parallel processing in the isoelectric focusing chip", Electrophoresis, 2003, vol. 24(21), pp. 3735-3744.

Zuo et al., "A method for global analysis of complex proteomes using sample prefractionation by solution isoelectrofocusing prior to two-dimensional electrophoresis", Analytical Biochemistry, 2000, vol. 284(2), pp. 266-278.

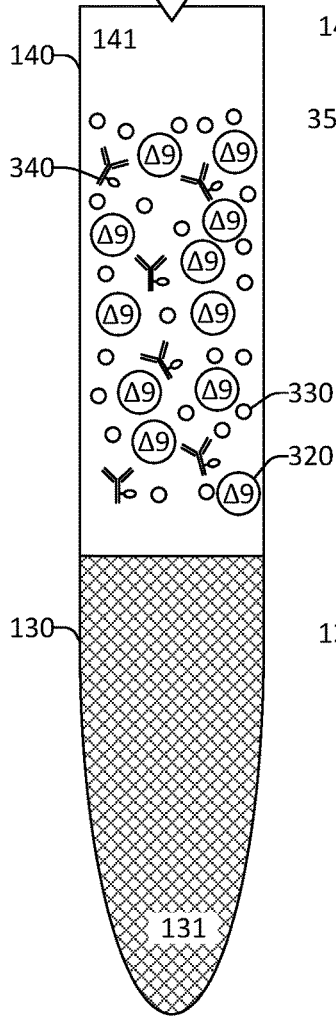
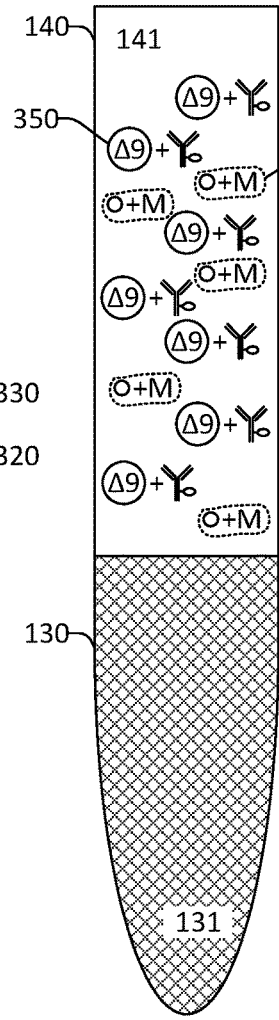
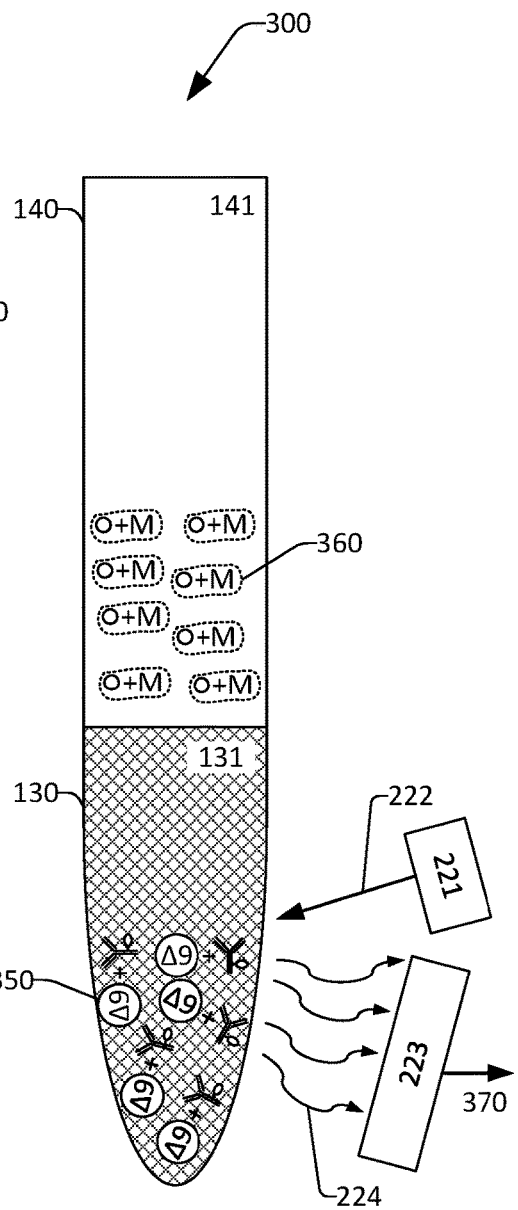
FIG. 3A  FIG. 3B  FIG. 3C
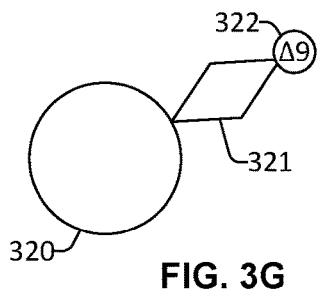
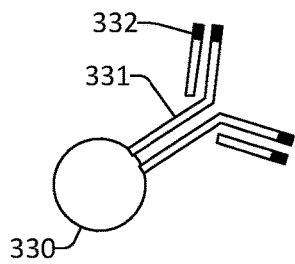
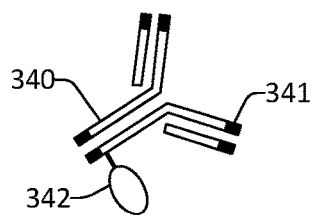
FIG. 3G  FIG. 3H  FIG. 3I

NO FLUORESCENCE OCCURS, NO FLUORESCENCE IS DETECTED BY DETECTOR 223

DETECTION OF METABOLITES FOR CONTROLLED SUBSTANCES

RELATED APPLICATIONS

This application is a divisional of prior U.S. patent application Ser. No. 14/957,405, filed on Dec. 2, 2015, which in turn claims priority to U.S. Provisional Patent Application No. 62/138,040, filed on Mar. 25, 2015, and entitled "METHOD FOR SELECTIVE DETECTION OF DELTA-9 THC ON MICROFLUIDIC DISCS", the entirety of each is incorporated herein by reference.

STATEMENT OF GOVERNMENTAL INTEREST

This invention was developed under contract DE-NA0003525 between National Technology & Engineering Solutions of Sandia, LLC and the U.S. Department of Energy/National Nuclear Security Administration. The U.S. Government has certain rights in this invention.

BACKGROUND

With the recent state-level legalization of the use of marijuana, several jurisdictions (e.g., Colorado, Washington) have passed regulations regarding the permissible levels of $(-)$-trans-$\Delta^9$-tetrahydrocannabinol ((6aR,10aR)-delta-9-tetrahydrocannabinol) (aka. delta-9-THC, delta-9, $\Delta 9$) in the blood. There are, however, no screening methods amenable to road-side law enforcement currently on the market which are specific for delta-9-THC.

Habitual users of marijuana can have high levels of tetrahydrocannabinol-based metabolites in their system, including delta-9-THC. Delta-9-THC is the active ingredient in marijuana capable of causing intoxication and therefore the target of interest for screening for intoxication. Delta-9-THC is rapidly converted in the body to other forms such as hydroxyl-THC and carboxy-THC. As the many forms of THC are lipophilic, the compounds are stored in fat cells and will gradually eliminate from the body over the course of several weeks. The short timeframe conversion of delta-9-THC compounds to metabolites, to the long timeframe elimination of the metabolites from the body of a habitual user, results in a small volume of delta-9-THC being present in the individual's body compared to the higher volume of metabolites being present. Current diagnostic screening tests (typically performed in urine for workplace drug testing) utilize reagents which seek to catch all forms of THC. In jurisdictions where marijuana is illegal this is an extremely convenient consequence, as significant levels of THC will be available for screening. However, in jurisdictions where marijuana is legal, any non delta-9-THC-based metabolites can interfere with accurate detection of levels of any delta-9-THC-based metabolites and compounds in an individual's bloodstream. In a habitual user's blood, the amount of metabolite can be thousands of times greater than an amount of delta-9 THC. The problem of detecting delta-9 THC is further exacerbated by the low levels of delta-9 THC in the bloodstream. Exemplary values for intoxication determination are in the states of Colorado, Montana, and Washington a person is considered intoxicated if the level of delta-9-THC in an individual's bloodstream is at, or exceeds, 5 nanograms/milliliter (ng/mL), and in Nevada, 2 ng/mL.

SUMMARY

The following is a brief summary of subject matter that is described in greater detail herein. This summary is not intended to be limiting as to the scope of the claims.

Various technologies presented herein relate to separating an analyte of interest from other compounds, wherein separation can be achieved by utilizing differences in densities of materials and fluids, and further, utilizing fluorophore-labelled compounds to identify location of the compounds and their binding to the analyte. In an embodiment, the analyte can be a marijuana-based compound or molecule (e.g., delta-9-THC). The various embodiments also enable extraction of the analyte from related compounds (e.g., metabolites). For example, it is possible that a habitual user of marijuana will have high levels of marijuana-related metabolites in their system. In marijuana, delta-9-THC is the active ingredient capable of causing intoxication and therefore the target of interest for screening for intoxication. Current diagnostic screening tests utilize reagents which seek to catch all forms of THC in a sample. Where marijuana use is restricted, finding THC is an indicator of marijuana usage. However, a level of delta-9-THC is required to determine impairment, whereby marijuana-based metabolites can interfere with accurate detection of levels of delta-9-THC in the bloodstream.

In an embodiment, a plurality of first beads having a first density and a plurality of second beads having a second density can be co-located in a first fluid, wherein the first density is higher than the second density. The first fluid can be located in a separation chamber, wherein the chamber has a closed end and an open end, a second fluid is located in the closed end, the first fluid is between the second fluid and the opening, and the second fluid has a higher density than the first fluid.

The first beads can have an analyte molecule respectively attached thereto (e.g., an analyte molecule is bound to a first bead), and further, an analyte in a test sample (e.g., a free analyte in a blood sample) can be added to the first fluid. A fluorescently-labelled analyte-specific antibody is also present in the first fluid and preferentially attaches to the free analyte from the test sample rather than the respective bound analyte molecules attached to the first beads. When no, or minimal, test sample analyte is present in the first fluid, the fluorescently-labelled analyte specific antibodies attach to the bound analyte molecules attached to the first beads. Upon application of a centrifugal force, the higher density first beads move to the second fluid. The second fluid can be irradiated (e.g., with light), and if any fluorescently-labelled analyte specific antibodies are bound to the first beads (e.g., via the bound analyte molecules) the chamber region of the second fluid will fluoresce. The magnitude of fluorescence can be utilized to indicate the presence of any analyte in the test sample, and accordingly, the bloodstream.

In an embodiment, if no free analyte (e.g., in freeform mode) is in the blood sample, the fluorescently-labelled analyte specific antibodies bind to the bound analyte of the first beads, and upon application of the centrifugal force and subsequent irradiation, the fluorescently-labelled analyte specific antibodies fluoresce in the second liquid. Based upon a level of fluorescence being higher than a threshold value (e.g., applied at a detector), a determination can be made that the blood sample does not contain an intoxicating level of analyte as the fluorescently-labelled analyte specific antibodies are bound to the analyte molecules attached to the first beads. Alternatively, if a level of fluorescence is less than the threshold value, a determination can be made that the blood sample does contain an intoxicating level of analyte as the fluorescently-labelled analyte specific antibodies are bound to the analyte molecules originating from the test sample, and accordingly, the fluorescent analyte specific antibodies are constrained to the chamber region of the first fluid and hence are not irradiated.

In an embodiment, the high density bead can be silica-based, the low density bead can be polymer-based (e.g., polystyrene), and the second fluid can be any of PERCOLL, dextran, poly(ethylene glycol), glycerol, sorbitol, iodixanol, cesium chloride, perfluorodecalin, etc.

The various embodiments relate to detection of a drug in general, e.g., based upon a presence of any compound related to the drug being detected. Further, the various embodiments can be utilized to extract a particular compound (an analyte, e.g., delta-9-THC) from other compounds of less interest formed either from the particular compound (e.g., metabolism of the analyte), or co-present with the analyte at the time of drug usage. Further, a metabolite can be identified in a test fluid, wherein the metabolite can be any of a cocaine-based compound, a methamphetamine-based compound, a methamphetamine compound, an amphetamine compound, an opiate-based compound, an MDMA-based compound, a ketamine-based compound, a PCP-based compound, a lysergic acid diethylamide-based compound, or a psilocybin-based compound.

The above summary presents a simplified summary in order to provide a basic understanding of some aspects of the systems and/or methods discussed herein. This summary is not an extensive overview of the systems and/or methods discussed herein. It is not intended to identify key/critical elements or to delineate the scope of such systems and/or methods. Its sole purpose is to present some concepts in a simplified form as a prelude to the more detailed description that is presented later.

BRIEF DESCRIPTION OF THE DRAWINGS

FIG. 3A illustrates an initial test condition where a test sample is added to a separation chamber, according to an embodiment.

FIG. 3B illustrates a condition in a separation chamber after an incubation period, according to an embodiment.

FIG. 3C illustrates a condition in a separation chamber after application of a centrifugal force, according to an embodiment.

FIG. 3G illustrates a schematic of a high density bead with a bound analyte attached thereto, according to an embodiment.

FIG. 3H illustrates a schematic of a low density bead with a metabolite specific antibody attached thereto, according to an embodiment.

FIG. 3I illustrates a schematic of an analyte specific antibody, wherein the antibody is labelled with a fluorophore, according to an embodiment.

DETAILED DESCRIPTION

Figure 1:
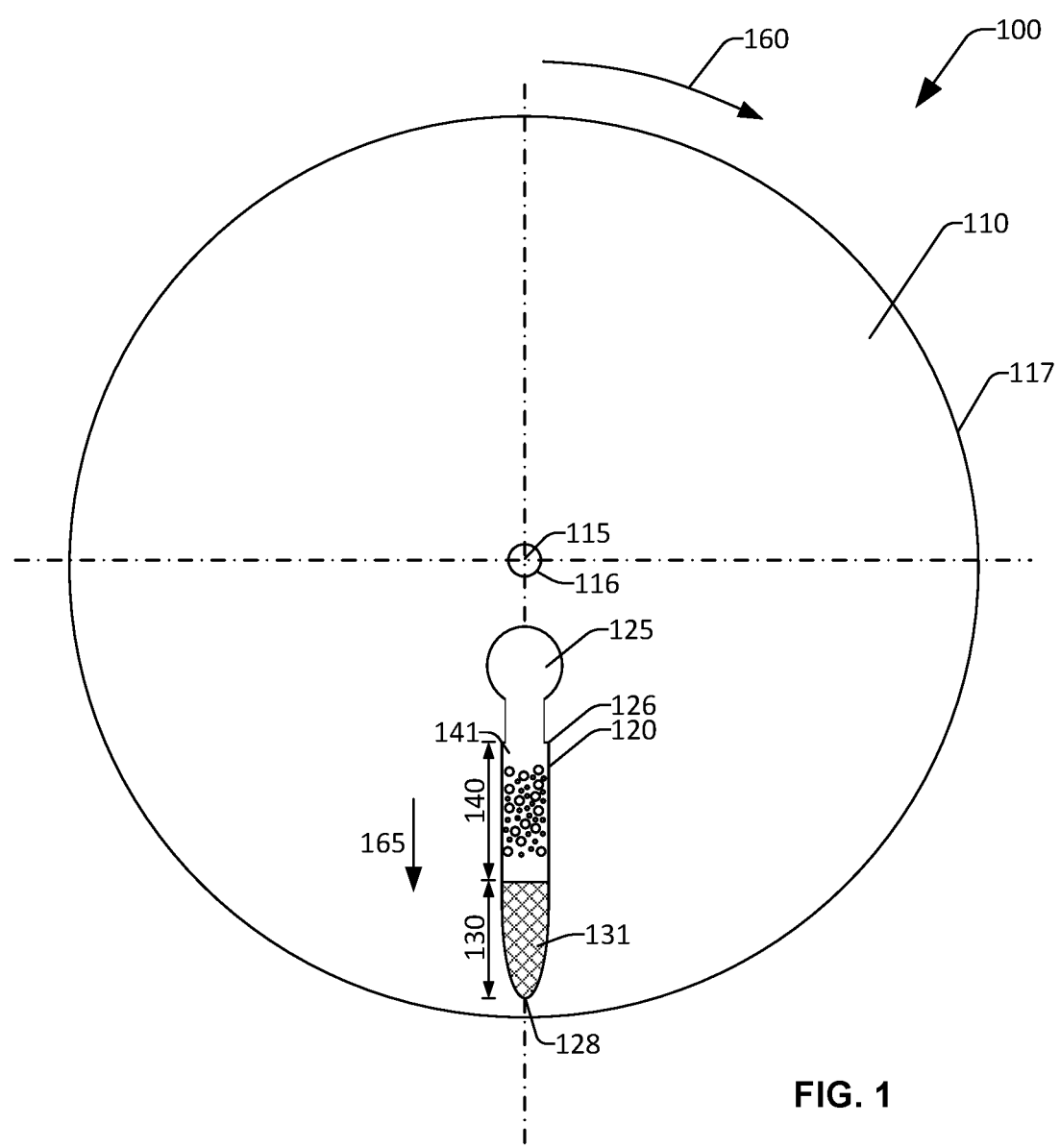
FIG. 1 is a schematic of a separation chamber located on a rotatable disk, according to an embodiment.

Various technologies pertaining to detecting a drug-related compound utilizing portable and relatively quick assaying system, are now described with reference to the drawings, wherein like reference numerals are used to refer to like elements throughout. In the following description, for purposes of explanation, numerous specific details are set forth in order to provide a thorough understanding of one or more aspects. It may be evident, however, that such aspect(s) may be practiced without these specific details. In other instances, well-known structures and devices are shown in block diagram form in order to facilitate describing one or more aspects.

As used herein, the terms "component" and "system" are intended to encompass computer-readable data storage that is configured with computer-executable instructions that cause certain functionality to be performed when executed by a processor. The computer-executable instructions may include a routine, a function, or the like. It is also to be understood that a component or system may be localized on a single device or distributed across several devices. The terms "component" and "system" are also intended to encompass hardware configured to cause certain functionality to be performed, where such hardware can include, but is not limited to including, Field-programmable Gate Arrays (FPGAs), Application-specific Integrated Circuits (ASICs), Application-specific Standard Products (ASSPs), System-on-a-chip systems (SOCs), Complex Programmable Logic Devices (CPLDs), etc.

Further, the term "or" is intended to mean an inclusive "or" rather than an exclusive "or". That is, unless specified otherwise, or clear from the context, the phrase "X employs A or B" is intended to mean any of the natural inclusive permutations. That is, the phrase "X employs A or B" is satisfied by any of the following instances: X employs A; X employs B; or X employs both A and B. In addition, the articles "a" and "an" as used in this application and the appended claims should generally be construed to mean "one or more" unless specified otherwise or clear from the context to be directed to a singular form. Additionally, as used herein, the term "exemplary" is intended to mean serving as an illustration or example of something, and is not intended to indicate a preference.

The various embodiments presented herein can be directed at detecting a plurality of drugs, chemical compounds, etc., wherein such compounds include compounds relating to (derived from, comprising, associated with) marijuana (e.g., tetrahydrocannabinol (THC), (−)-trans-$\Delta^9$-tetrahydrocannabinol ((6aR,10aR)-delta-9-tetrahydrocannabinol, delta-9-THC, $\Delta$9-THC, etc.), methamphetamine, amphetamine, cocaine, opiates (e.g., heroin, opium), MDMA (3,4-methylenedioxy-methamphetamine), ketamine, PCP (1-(1-phenyl cyclohexyl)piperidine), PCP analogs, lysergic acid diethylamide (LSD), psilocybin, etc.

As previously mentioned, in the United States, one jurisdiction may consider a drug to be illegal, while another jurisdiction regards the drug as being legal. For example, a number of states have passed legislation legalizing the use of marijuana, while at the Federal level, marijuana is still legally restricted. Hence, in one jurisdiction, identifying any compound relating to, or derived from, marijuana is sufficient to arrest a person for partaking in suspected drug use. However, in a state where marijuana usage is legalized, rather than attempting to detect whether a person has used marijuana, the focus is on determining whether a person is under the influence of marijuana, and in particular, whether the person has a higher than legal amount of delta-9-THC currently in their body. Eventually the delta-9-THC compound metabolizes to form a metabolite, wherein the metabolite is not a psychoactive compound, and subsequently the metabolite is flushed out of the body. Hence, rather than simply making a determination that a person has smoked marijuana, a detection system is required that of all the compounds (at least 483 have been identified) which may be present in an individual's body from smoking marijuana, the system is able to detect the delta-9-THC compound in the background noise of one or more metabolites. Further, the detection of the delta-9-THC is not obscured by the other compounds leading to false positive test results.

A particular time at which a timely and accurate determination of marijuana use is important is during operation of a machine, vehicle, etc., by an individual who may have recently smoked marijuana, and accordingly may be attempting to drive a vehicle while under the influence of the psychotic effects of delta-9-THC. Hence, a system that can be utilized in a roadside stop (e.g., a sobriety checkpoint, being pulled over for erratic driving, etc.) to assess the current state of an individual would be highly beneficial to law enforcement personnel. Hence, such a system should be portable, provide a timely assessment (e.g., timely provide a level of delta-9-THC in a driver's blood), and further, should be easy to implement by a police officer, or other law enforcement personnel, test person, etc.

FIG. 1 is a schematic illustration of a microfluidic disk 100 arranged in accordance with embodiments of the present invention. The microfluidic disk 100 comprises a substrate 110, wherein the substrate 110 has a center 115, at which can be positioned a locating hole 116 for positioning the disk 100 on a motor to be spun. The disk 100 has a periphery 117.

A chamber 120 (e.g., a microfluidic channel, a microchannel, a cell, etc.), which can be utilized as a separation chamber, is located on the disk 100. The microfluidic disk 100 further includes a fluid inlet port 125 in fluid communication with the chamber 120, wherein the fluid inlet port 125 is located nearer to the center 115 of the disk 110 than the chamber 120, wherein the chamber 120 is located between the port 125 and the disk periphery 117. During operation, as will be described further below, a fluid, e.g., a biological fluid, such as blood, whole blood, serum, saliva, urine, or any other suitable sample matrix, can be added to the chamber 120 via the inlet port 125. A first end, an open end 126, of the chamber 120 connects to the port 125. It is to be appreciated that the relative sizes and proportions of the various components illustrated in FIG. 1 are simply to enable understanding of the various embodiments and concepts presented herein, and respective proportions of a first feature to a second feature can be different to that illustrated.

A second end, end 128 of the chamber 120, is a closed end, wherein the end 128 is located closer to the periphery 117 at an opposite end of the chamber 120 to the open end 126 of the chamber 120 (e.g., the end 128 is proximate to the disk periphery 117 and the open end 126 is proximate to the center 115 of the disk).

The chamber 120 can comprise two portions, a first portion 130 (first layer which includes a first fluid 131) which is located at the end 128 of the chamber 120, wherein the first portion 130 is located in the chamber 120 furthest from the open end 126. The first portion 130 is a testing area, e.g., is utilized to assay a sample for a particular compound of interest. A second portion 140 (second layer which includes a second fluid 141) is located at the end of the chamber 120 nearest the open end 126. The fluid 131 has a higher density than the fluid 141, wherein the difference in fluid densities can be utilized to separate out one or more components, e.g., separate first beads having a first density from second beads having a second density, wherein the first density is higher than the second density, as further described.

The second fluid 131 can be formed from any suitable material. In an embodiment, the second fluid 131 can be a colloidal suspension of silicon nanoparticles (e.g., PERCOLL) with a density of about 1.4-1.6 g/cm$^3$. Surfactants and salts can be added to stabilize any biological reactions (e.g., with 0.05% (weight/volume) Tween-20, 0.15M sodium chloride, 0.02M sodium phosphate, pH 7.4-8.5. Further, the second fluid can be dextran, poly(ethylene glycol), glycerol, sorbitol, iodixanol, cesium chloride, perfluorodecalin, etc.

As further described herein, the disk 100 can be rotated, e.g., in direction 160, such that a centrifugal force is generated, e.g., in direction 165, wherein the centrifugal force in direction 165 acts on one or more components (e.g., fluids 131 and 141, first beads, second beads, etc.) located in the chamber 120 to facilitate separation of a component (e.g., a compound) from a plurality of other components that are also located in the chamber 120. In an exemplary embodiment, centrifugal separation can be utilized to separate a delta-9-THC compound(s) from a plurality of metabolites formed either from a previously existing delta-9-THC compound or other cannabinoid. In another example, an antibody which has bound to an analyte can be separated from a sample to enable determination of whether an individual is using a restricted drug, e.g., a class 1 drug.

The substrate 110 may be formed from any suitable material. In an embodiment, the substrate 110 may be a quartz substrate. In another embodiment, quartz, glass, polycarbonate, fused-silica, PDMS, or other transparent substrate can be utilized to enable optical observation of sample within the chamber 120 of the disk 100. In another embodiment, the disk 100 can be formed from a polymer, a metal, a semiconductor substrate, etc. In another embodiment, multiple materials can be utilized in combination to form the disk 100. Further, any suitable surface treatment, coating, etc., can be utilized, where the coating, etc., can enhance compatibility with a fluid(s) placed on the substrate 110. In another embodiment, a surface treatment, coating, etc., can be utilized to control interaction of a fluid with the substrate 110. It is to be appreciated that while FIG. 1 illustrates the substrate 110 as being circular in form, the substrate 110 can have any shape, size, thickness, etc., to enable any embodiment presented herein, e.g., the substrate 110 can have a square profile.

The substrate 110 may generally, at least partially, define a variety of microfluidic features. Generally, microfluidic, as used herein, refers to a system, device, or feature having a dimension of about 1 mm or less and suitable for at least partially containing a fluid. In another embodiment, a microfluidic dimension can be about 500 µm or less. In a further embodiment, a micro fluidic feature can have a dimension of about 100 µm or less. Other dimensions may be used. The substrate 110 may define one or more micro fluidic features, including any number of chambers, channels, inlet/outlet ports, another feature(s), etc.

Microscale fabrication techniques, generally known in the art, may be utilized to fabricate the microfluidic disk 100. The microscale fabrication techniques utilized to fabricate the disk 100 may include, for example, embossing, etching, injection molding, surface treatments, photolithography, bonding and other techniques.

As previously mentioned, a fluid inlet port 125 can be provided to receive a test sample (test fluid) to be analyzed using the microfluidic disk 100. The fluid inlet port 125 can have generally any configuration, and fluid may enter the fluid inlet port 125 utilizing substantially any fluid transport mechanism, including dropping, pipetting, or pumping a fluid sample into the fluid inlet port 125. The fluid inlet port 125 can take substantially any shape. Generally, the fluid inlet port 125 is in fluid communication with the chamber 120. Generally, by fluid communication it is meant that a fluid may flow from one area to the other (e.g., from the port 125 to the chamber 120), either freely or using one or more transport forces and/or valves, and with or without flowing through intervening structures.

It is to be appreciated that while a single chamber 120 is illustrated as being present on the disk 110, any number of chambers 120 can be present on the microfluidic disk 110, e.g., to facilitate a plurality of tests to be conducted at the same time.

As the microfluidic disk 100 is rotated in the direction indicated by the arrow 160 (or in the opposite direction), a centrifugal force may be generated. The centrifugal force may generally transport fluid (or a bead, etc.) from a first portion (first layer) of the chamber 120 to a second portion (second layer).

Figure 2:
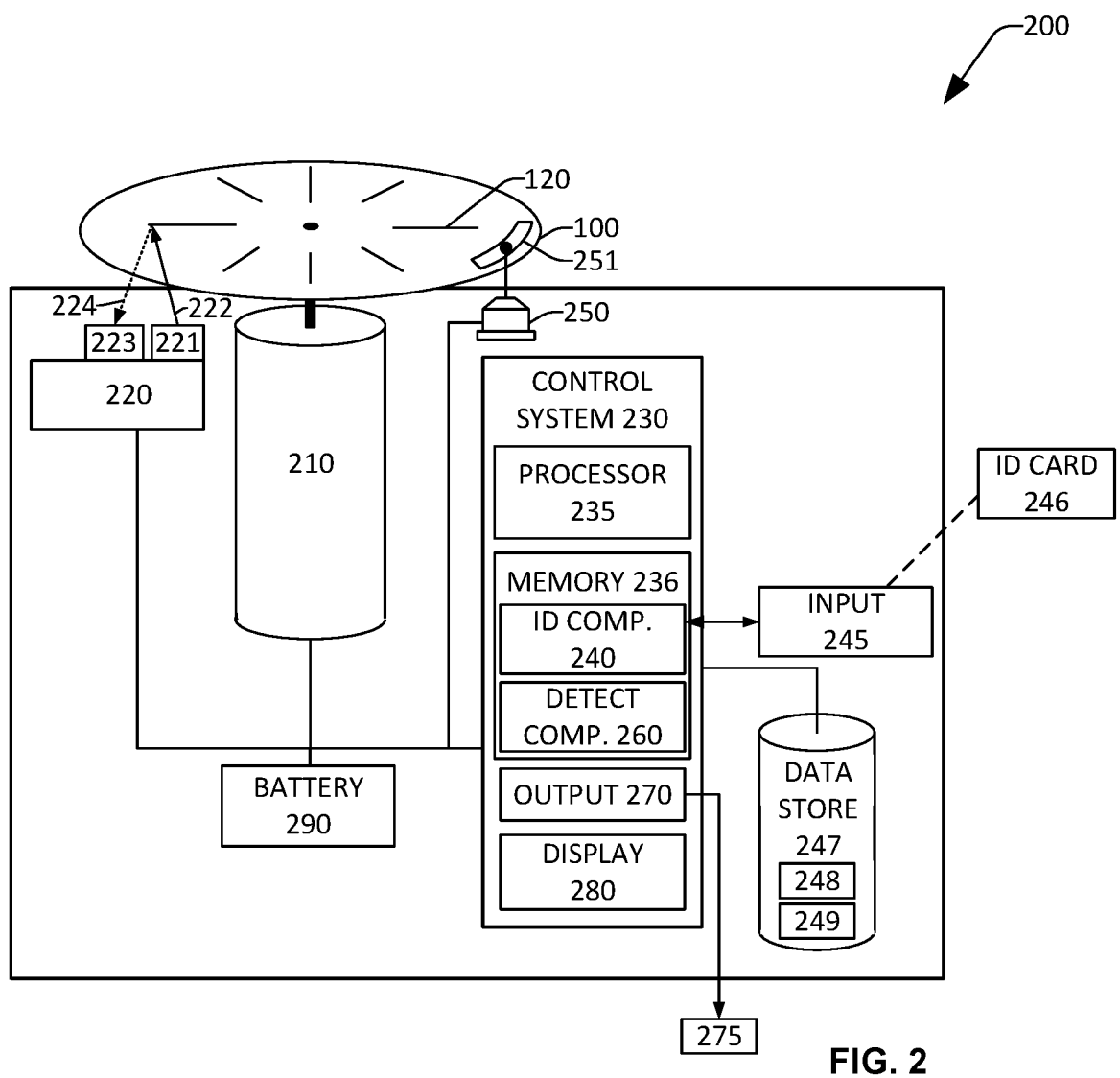
FIG. 2 is a schematic of a system that can be utilized to determine whether a compound is in a particular location in a separation chamber, according to an embodiment.

FIG. 2 illustrates a drug detection system 200 which can be utilized to process a sample, and determine whether a drug-related compound is present in the sample. The drug detection system 200 includes the disk 100 of FIG. 1, with one or more chambers 120 located thereon. A motor 210 is coupled to the disk 100 and configured to spin the disk 100, generating a centrifugal force(s). A detection module 220 is positioned to detect (or determine an absence of) a signal generated by, for example, a labeled antibody located in the layer 130 (e.g., location of a labeled antibody in a test region formed by layer 130), as described further herein. A plurality of detection techniques can be utilized for the various embodiments presented herein. For example, an optical detection technique, e.g., fluorescence, luminescence, absorbance, time-resolved fluorescence, refractive index monitoring, etc., an electrochemical technique, an amperometric technique, etc. As further described, in an exemplary embodiment, an antibody can be labeled or tagged, e.g., to fluoresce, when stimulated by light during a detection process, thereby enabling a location of the antibody to be determined (e.g., in the layer 130), and accordingly, whether a drug compound is present (or not) with the antibody. It is to be appreciated that any suitable tag can be utilized, for example, organic dyes (e.g., cyanine dye, ALEXAFLUOR, fluorescein, fluorescein isothiocyanate, etc.), inorganic quantum dots (e.g., cadmium selenide quantum dots), polystyrene nanoparticles (e.g., FLUOSPHERES), organometallic dyes (e.g., europium-based dyes), etc., as described further, an emitter and a sensor can be selected based upon the tag system selected.

In another embodiment, the lack of presence of the fluorescing antibody at a particular location (e.g., in the layer 130) can be an indication that a drug compound is present in a sample. To enable assaying of a sample by the one or more available techniques, the detection module 220 can include an emitter 221 and a sensor 223. Continuing the example of the antibody that is configured to fluoresce, the emitter 221 can be a light source configured to transmit light 222 in accordance with a stimulation frequency of the fluorescent antibody, and further the sensor 223 can detect light 224 transmitted (emitted, reflected, generated) from the antibody as a function of the fluorescence process. E.g., the emitter 221 and sensor 223 comprise a laser and optics suitable for optical detection of fluorescence from fluorescent labels (e.g., as applied to an antibody). In another example, other detectors, such as electronic detectors, may be used.

In an embodiment, a plurality of emitters 221 can be included in the system 200, and similarly, a plurality of sensors 223 can also be included, wherein the emitters 221 and sensors 223 can be selected for use based upon the type of drug being tested for, a detection labeling of a component under test, e.g., a labeled antibody, etc. Hence, by utilizing a plurality of co-located emitters 221 and sensors 223, a single system 200 can be utilized to test for a plurality of different drug-related compounds.

The drug detection system 200 further includes a control system 230 that is configured to control operation of the drug detection system 200. The control system 230 includes a processor 235 and a memory 236. The memory 236 includes components that are executable by the processor 235, wherein functionalities of the processor 235, when executing the components, are described below.

The memory 236 includes an identification component 240 which can be configured to obtain and store identification data regarding an identification of an individual who is undergoing testing. The identification component 240 can be configured to receive information from a data input component 245, wherein the data input component 245 can be a card reader configured to read identification information from an identification card 246, e.g., a driver's license. Further, the data input component 245 can further include an input device such as a keypad and display, wherein information is entered to complete data fields, respond to questions and data prompts, etc. Data collected by the input component 245 can be stored in a data store 248. In an embodiment, the identification data can be utilized to uniquely mark a disk 100, e.g., for subsequent analysis. For example, a first chamber on the disk 100 can be utilized to conduct a drug test, while a second chamber can be utilized to store a blood sample which can be utilized for subsequent testing, e.g., a roadside test conducted with the drug detection system 200 generates a positive result, and an individual may be operating a vehicle while under the influence of an illegal drug. A stored blood sample can be utilized to conduct subsequent testing, e.g., at a testing center having equipment available that has a higher degree of accuracy to determine a drug in a sample. A labeling component 250 can be utilized to label the disk 100 with information (e.g., as obtained from the input component 245) to enable unique identification of the disk 100. In an embodiment, the disk 100 can have a writeable region included therein, e.g., similar to a writeable region on a writeable compact disk. Alternatively, the labeling component 250 can be a printing head to print data onto a surface of the disk 100. Further, the labeling component 250 can be a laser device that can burn data onto a surface of the disk 100.

A detection component 260 is further included in the memory 236, wherein the detection component 260 can be utilized to configure operation of the system 200. For example, an input can be received (e.g., via input component 245) regarding a particular type of drug that is to be tested for, and the detection component 260 can select the required emitter 221 and sensor 223 to assay for the particular analyte. Further, the detection component 260 can provide instructions to the person operating the system 200 (e.g., a police officer) to assist the person in correctly performing the test. In another embodiment, the detection component 260 can co-ordinate operation of the various devices of the system 200. For example, a chamber 120 on the disk 100 can have a test sampled added thereto, and to initiate processing the disk 100 can be inserted into the system 200 (e.g., by a disk drawer, not shown). Once the disk 100 is located in the system 200, e.g., the disk 100 is located on the motor 210, a timer (not shown) can be initiated to control a duration of incubation of the sample within the chamber 120. Upon completion of the incubation period, the sample in the chamber 120 can undergo testing, results generated therefrom, etc. The various operations required to initiate a test through to test completion can be controlled by the detection component 260.

An output component 270 can be utilized to generate a test result 275 and transmit the test result 275 to an external system. Further, a display 280 (e.g., a touchscreen) can be further included in the system 200 to facilitate display of results, presentation of interactive screens, receive input information, etc. A battery 290 can be further included in the system 200 to enable power to, and operation of one or more components included in the system 200, e.g., the computing system 230, the motor 210, the detector component 220, etc. All or selected components illustrated in FIG. 2 can be housed in a common housing. Microfluidic disks 100 may be placed on the motor 210 and removed, such that multiple disks may be analyzed by the system 200.

The motor 210 can be a centrifugation and/or stepper motor. The motor 210 can be positioned relative to the detection module 220 such that, when the disk 100 is situated on the motor 210, the disk 100 is positioned such that a detection region (e.g., the layer 130) of the chamber 120 is exposed to the detection module 220.

In another example, although not explicitly shown in FIG. 2, one or more actuators can be coupled to the motor 210 and/or disk 100 such that the disk 100 is moved relative to the detection module 220 responsive to signals from the processor 235. The processor 235 can provide a control signal(s) to the motor 210 to rotate the disk 100 at a selected speed(s) for a selected time(s). The processor 235 can provide a control signal(s) to the detection module 220, wherein the control signal controls which emitter 221, sensor 223, etc., are to be used.

FIGS. 3A-3F, schematics 300 and 301, illustrate embodiments for detecting the presence of a drug and/or its metabolites. As previously mentioned, habitual users of marijuana will have high levels of metabolites in their system. In marijuana, delta-9-THC is the active ingredient capable of causing intoxication and therefore the target of interest for screening for intoxication. Beads having different densities in combination with antibodies specific for delta-9-THC and antibodies for metabolites can be utilized to separate delta-9-THC compounds from metabolites. In an embodiment, the respective concentration of first beads to second beads can be tuned such that there are sufficient metabolite-specific binding sites to effectively deplete the metabolite but not so much that potential cross-reactivity with delta-9-THC depletes a desired signal (e.g., during concentration measurement and determination by the detection module 220).

FIGS. 3A-3C illustrate an embodiment 300 for when a sample does not contain any delta-9-THC. FIG. 3A illustrates a sample 310 is added to the fluid 141 in the chamber 120, wherein the sample 310 is taken from an individual who has not recently consumed marijuana and hence has only metabolites (M) in their blood. The first layer 140 includes a fluid 141 comprising a first plurality of beads 320 having a first density, and a second plurality of beads 330 having a second density, and an analyte specific antibody 340. As previously mentioned, the first density of a first bead 320 is higher than the second density of a second bead 330.

Further, as shown in FIG. 3G, the first bead 320 has a first protein 321 attached thereto, wherein the first protein 321 is configured to be delta-9-THC specific, such that a delta-9-THC molecule 322 is attached to the first bead 320 via the first protein 321. Per FIG. 3H, the second bead 330 has an antibody 331 attached thereto, wherein the antibody 331 is configured to be specific to (e.g., bind to) the metabolites (e.g., non-delta-9-THC specific) via the regions 332.

Further, as shown in FIG. 3I, the antibody 340 has regions 341 which are configured to be specific to a delta-9-THC molecule, and further has a fluorophore 342 attached thereto. As further described, detecting the presence of the antibody 340 by its fluorophore 342 in region 130 (e.g., based upon its attachment to a first bead 320) enables determination of whether a blood sample includes delta-9-THC.

The beads 320 and 330 can be selected from any suitable materials, e.g., wherein a selected material is inert with respect to reacting with a delta-9-THC molecule(s). Example materials include silica (and associated materials, e.g., glass, hollow glass spheres, etc.), polystyrene, polystyrene divinyl benzene, poly(methyl methacrylate), superparamagnetic particles such as polystyrene particles compounded with metal nanoparticles, metals such as gold, silver, iron, polyamide, melamine, etc. As mentioned, the respective materials can be selected based upon (a) a difference in density, wherein the first plurality of beads 320 have a density that is greater than a density of material 131 comprising the first layer 130, and the second plurality of beads 330 have a density that is less than the density of the material 131 comprising the first layer 130. In an example embodiment, the first beads 320 can be formed from silica (e.g., having a density of about 1.8-2.0 $g/cm^3$), and the second beads 330 are formed from polystyrene (e.g., having a density of about 1.0 $g/cm^3$, or less).

It is to be appreciated that while the first beads 320 are illustrated as being of a different size to the second beads 330, this is purely for the purposes of illustration and understanding. The first beads 320 and the second beads 330 can be of the same size, or of a different size, e.g., the first beads 320 can be smaller than the second beads 330. The first beads 320 and the second beads can have a size ranging from about 0.1 micrometers to about 50 micrometers.

As shown in FIG. 3B, after an incubation period has expired, the antibodies 340 are attached to the first beads 320, forming a first bead combination 350. Further, the metabolites M are attached to the second beads 330, forming a second bead combination 360. Attachment of the antibodies 340 to the first beads 320 results from the delta-9-THC molecule specific regions 341 binding with the delta-9-THC molecule 322 is attached to the first bead 320. Hence, the respective fluorophores 342 of the respective antibodies 340 are attached to respective beads 320, wherein the beads 320 have the first density.

At FIG. 3C, the chamber 120 and contents therein can be rotated by the motor 210, thereby subjecting the chamber 120 and the contents therein to a centrifugal force. Application of the centrifugal force causes the first bead combination 350 and the second bead combination 360 to move in a radial direction (e.g., direction 165 of FIG. 1). Owing to the density of the first beads 320 being greater than a density of the layer material 131, the first beads 320 (and the respectively attached antibodies 340) are able to enter the layer 130 in the closed end portion of the chamber 120. However, owing to the density of the second beads 330 being less than the density of the first layer 130, the second beads 330 (and the respectively attached metabolites M) are not able to pass into the layer 130 in the closed end portion of the chamber 120, and are, accordingly, constrained by the layer 130 to remain in the fluid 141.

In the example presented in FIGS. 3A-3C, when stimulated by an electromagnetic energy (e.g., a light) the respective fluorophores 342 of the respective antibodies 340 will fluoresce. Hence, a light source 221 (e.g., can be located proximate to the chamber region 130 comprising the fluid 131 and first bead combination 350) can emit a light 222, where the light 222 is directed towards the beads 320 and the attached antibodies 340. Upon stimulation by the light 222, the fluorophores 342 fluoresce, with emitted light 224 generated by the fluorescence effect being captured and/or detected by a detector 223. The detector 223 can be configured to generate a signal 370 indicating any of a magnitude of fluorescence measured by the detector 223, whether any fluorescence was measured (e.g., a simple binary signal, 1=fluorescence detected, 0=no fluorescence detected), etc.

In an embodiment, the magnitude of the signal 370 is such that a determination can be made that a high proportion (e.g., a majority) of fluorophore-labelled antibodies 340 originally in the second fluid 141 at the moment that the blood sample 310 was added, are now located in the first fluid 131, and accordingly, the delta-9-THC specific antibodies 340 were only able to attach to the delta-9-THC molecules 322 attached to the beads 320. Hence, based upon such determination, it is possible to identify blood sample 310 as having no delta-9-THC molecules present, or, it is possible to identify blood sample 310 as having a level of delta-9-THC molecules present that is below a given legal limit.

Figure 3D:
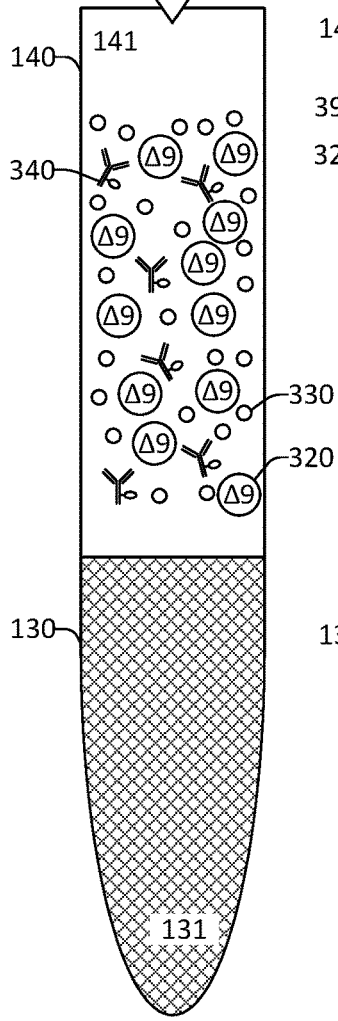
FIG. 3D illustrates an initial test condition where a test sample is added to a separation chamber, according to an embodiment.
Figure 3E:
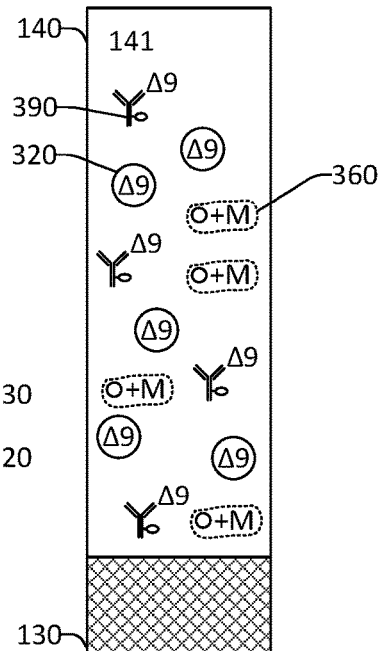
FIG. 3E illustrates a condition in a separation chamber after an incubation period, according to an embodiment.
Figure 3F:
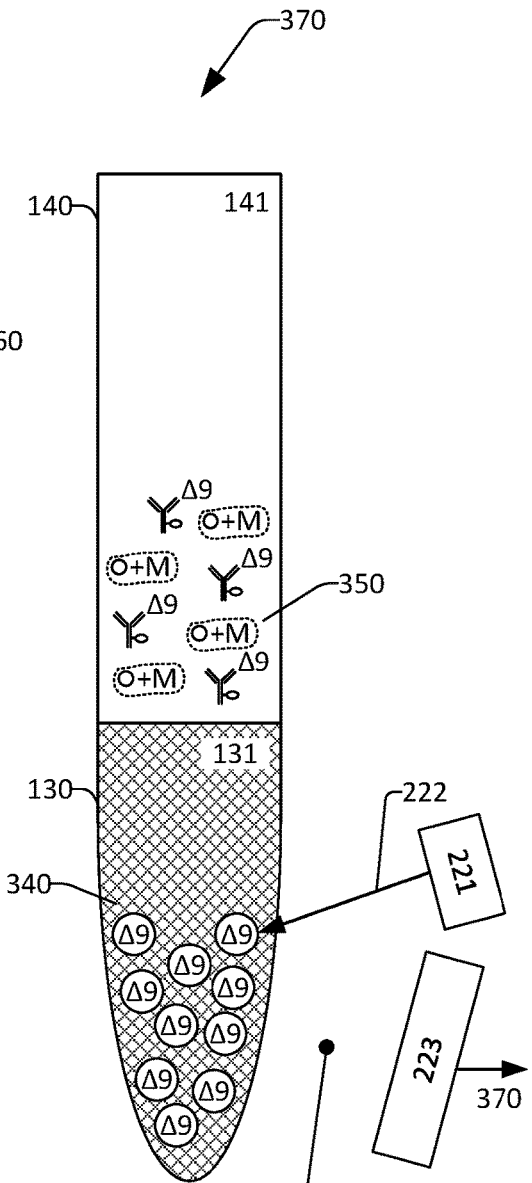
FIG. 3F illustrates a condition in a separation chamber after application of a centrifugal force, according to an embodiment.

Turning to FIGS. 3D-3F, an example scenario 301 is illustrated where a sample does contain delta-9-THC (e.g., the volume of delta-9-THC present is above a legal limit). FIG. 3D illustrates a sample 380 is added to the fluid 141 in the chamber 120, wherein the sample 380 is taken from an individual who has recently consumed marijuana and hence has both delta-9-THC molecules (Δ9) and metabolites M in their blood. As previously described with regard to FIG. 1, at the time of adding a blood sample to the second layer 140, the second fluid 141 comprises a first plurality of beads 320 with delta-9-THC molecules 322 attached thereto by a protein 321, a second plurality of beads 330 having the metabolite specific antibodies 331 attached thereto, and a plurality of delta-9-THC specific antibodies 340. As previously mentioned, the first density of a first bead 320 is higher than the second density of a second bead 330.

As shown in FIG. 3E, after an incubation period has expired, the antibodies 340 are attached to the Δ9 molecules, forming an antibody combination 390. Further, the metabolites M are attached to the second beads 330, forming the second bead combination 360. Owing to the Δ9 molecules being attached to the plurality of delta-9-THC specific antibodies 340, there are no (or a minimal number of) delta-9-THC specific antibodies 340 attached to the delta-9-THC molecules 322 of the first beads 320. Hence, there are no fluorophores 342 of the respective antibodies 340 attached to respective beads 320.

At FIG. 3F, the chamber 120 and contents therein can be rotated by the motor 210, thereby subjecting the chamber 120 and the contents therein to the centrifugal force. Application of the centrifugal force causes the first beads 320, the second bead combinations 360, and the antibody combinations 390 to move in a radial direction (e.g., direction 165 of FIG. 1). Owing to the density of the first beads 320 being greater than a density of the layer material 131, the first beads 320 are able to enter the layer 130 in the closed end portion of the chamber 120. However, owing to the density of the second beads 330 being less than the density of the first layer 130, the second beads 330 (and the respectively attached metabolites M) are not able to pass into the layer 130 in the closed end portion of the chamber 120, and are, accordingly, constrained by the layer 130 to remain in the fluid 141. Further, the density of the first layer material 131 is higher than a third density of the antibody combinations 390, and thus the antibody combinations 390 are not able to pass into the layer 130 in the closed end portion of the chamber 120, and are also constrained by the layer 130 to remain in the fluid 141. Thus, the fluorophores 342 of the respective antibodies 340 are confined to the fluid 141.

Hence, contrary to the fluorescence of the fluorophores 342 occurring in FIG. 3C, when the arrangement presented in 3F is stimulated by the electromagnetic energy of the light 222, no light 224 is emitted as there are no fluorophores 342 present in the liquid 131. Hence, there is no fluorescence effect being captured and/or detected by the detector 223, and accordingly the signal 370 indicates no fluorescence was detected, e.g., the signal 370 can have a value of 0=no fluorescence detected.

In an embodiment, the magnitude of the signal 370 is low or non-existent such that a determination can be made that no, or a very small number of (e.g., a minority), fluorophore-labelled antibodies 340 originally in the second fluid 141 at the moment that the blood sample 310 was added, are located in the first fluid 131, and rather the majority of fluorophore-labelled antibodies 340 are confined to fluid 141. The majority of fluorophore-labelled antibodies 340 are attached to the Δ9 molecules from the blood sample 380. Hence, based upon such determination, it is possible to identify blood sample 380 as containing a volume of delta-9-THC molecules (e.g., the Δ9 molecules) that is above a given legal limit.

With reference to FIGS. 3D-F in comparison with FIGS. 3A-C, a fluorophore-labelled antibody 340 will preferentially bind with a 'free' Δ9 molecule from the blood sample 380, than it will with a delta-9-THC molecule 322 attached to the first bead 320. Hence, the preferential binding can be utilized to control where the fluorophore-labelled antibody 340 will be after application of the centrifugal force. For a blood sample containing no, or few, Δ9 molecules (e.g., blood sample 310), after application of the centrifugal force, the fluorophore-labelled antibody 340 is located in the density material 131 (e.g., attached to a first bead 320). For a blood sample containing a high volume of Δ9 molecules (e.g., blood sample 380), after application of the centrifugal force, the fluorophore-labelled antibody 340 is located in the low density material 141 (e.g., attached to a Δ9 molecule).

With reference to both sets of FIGS. 3A-3C and 3D-3F, presence of the metabolites M can be reduced by binding the metabolite molecules to the metabolite specific antibodies 331 on the beads 330. Hence, while it is possible for the metabolites M to also bind to the delta-9-THC specific antibodies 340, the effect can be reduced by including the metabolite specific antibodies 331 into the liquid 141.

In another embodiment, to reduce a volume of metabolite present in a sample, the metabolite can be removed prior to determination of a presence of delta-9-THC compounds. For example, a sample can be incubated in a separation chamber with metabolite-specific antibodies attached to low density beads (e.g., metabolite specific antibodies 331 attached to the beads 330). After incubation, the disk, upon which the sample chamber is located, can be spun and a separation step screens out the polystyrene beads. The metabolite-reduced sample can now be reincubated with beads comprising the delta-9-THC molecules (e.g., the first beads 320 with the attached delta-9-THC molecules 322), as described in FIGS. 3A-3F. This two-stage incubation enables greater specificity and sensitivity by isolating the important detection immunoassay from the depletion step. The two-stage incubation can be utilized where the antibody for the analyte is not 100% specific. For example, the antibody for the delta-9-THC is also approximately 20% cross-reactive with a metabolite, hence to eliminate the possibility of a false positive from a test, by removing the metabolite during a first incubation, and adding the analyte-specific antibody as part of a second incubation, any free metabolite has been bound to the first antibody, thereby negating the problem of a cross-reaction.

Figure 4A:
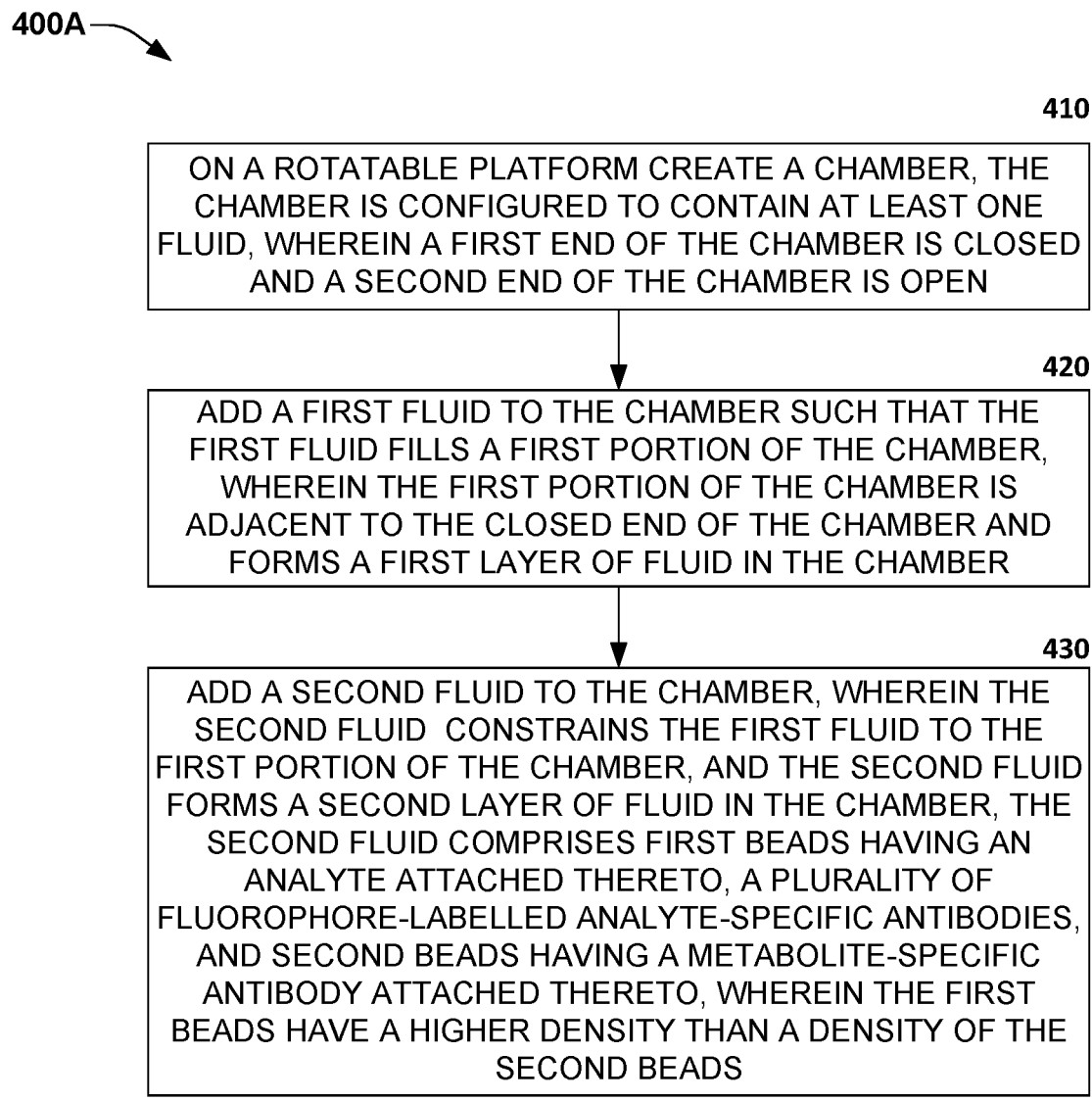
FIG. 4A is a flow diagram illustrating an exemplary methodology for fabricating a disk comprising a density separation chamber(s).
Figure 4B:
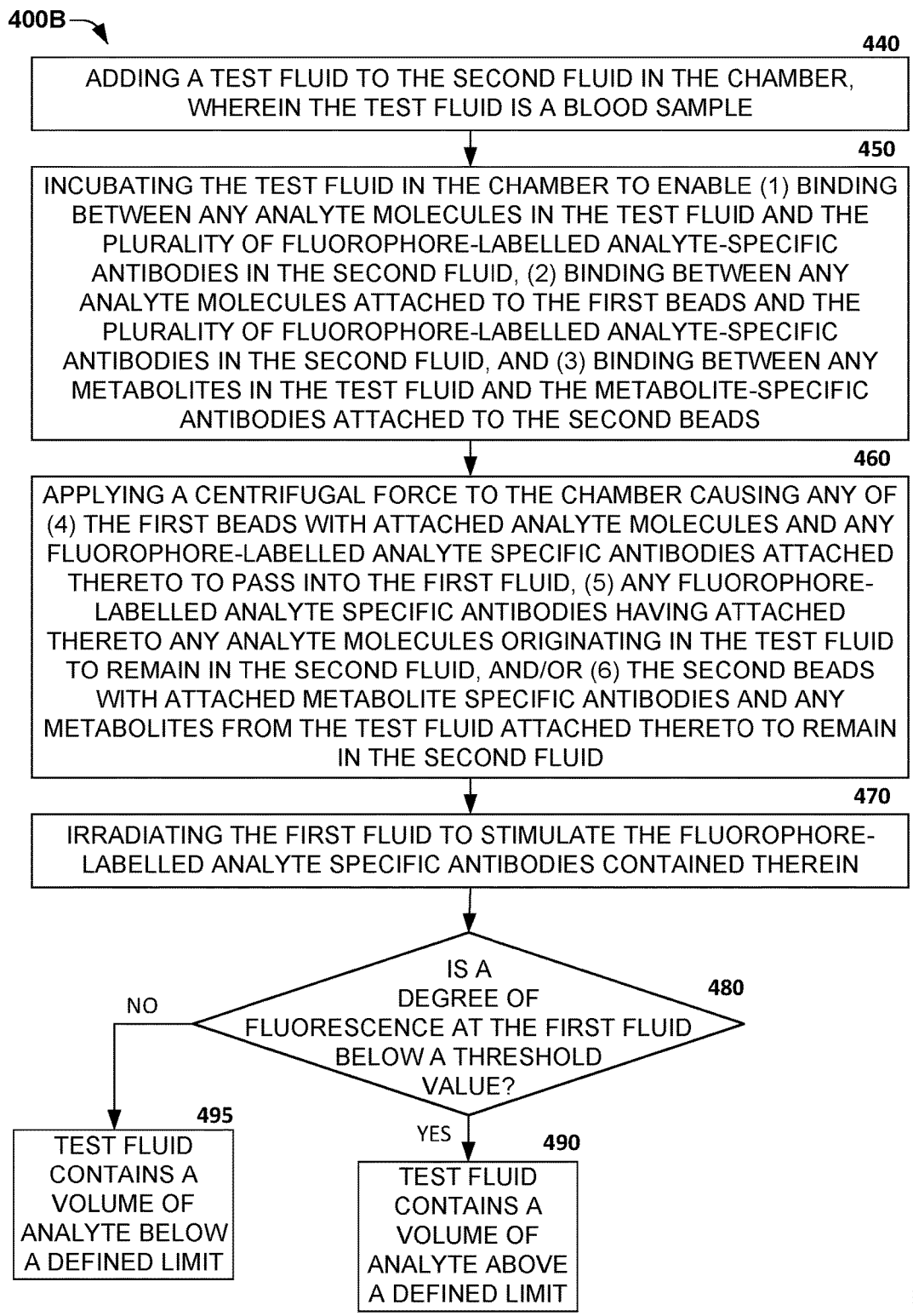
FIG. 4B is a flow diagram illustrating an exemplary methodology for extracting an analyte from a sample.

FIGS. 4A and 4B illustrate exemplary methodologies relating to utilizing centrifugal force separation to detect presence of an analyte in a fluid. In an embodiment, the analyte can be a delta-9-THC molecule(s), and the fluid is a blood sample. While the methodologies are shown and described as being a series of acts that are performed in a sequence, it is to be understood and appreciated that the methodologies are not limited by the order of the sequence. For example, some acts can occur in a different order than what is described herein. In addition, an act can occur concurrently with another act. Further, in some instances, not all acts may be required to implement the methodologies described herein.

FIG. 4A illustrates a methodology 400A for fabricating a rotatable disk having a plurality of separation chambers located thereon. At 410, one or more separation chambers are fabricated, wherein each chamber in the plurality of separation chambers is configured to contain at least one fluid, wherein a first end of the chamber is closed and a second end of the chamber is open.

At 420, a first fluid is added to each chamber in the plurality of separation chambers such that the first fluid fills a first region of the each respective chamber. The first region of each chamber is located at the closed end of each respective separation chamber.

At 430, a second fluid is added to each chamber in the plurality of separation chambers such that the second fluid confines the first fluid to the first region of each respective chamber, and the second fluid is confined to a second region of each separation chamber, the second region being adjacent to the open ended portion of each chamber. The second fluid comprises: first beads having an analyte attached thereto, second beads having a metabolite-specific antibody attached thereto, and a plurality of analyte specific antibodies. The first beads have a higher density than a density of the second beads. Each respective analyte specific antibody in the plurality of analyte specific antibodies is labelled with a fluorophore.

FIG. 4B illustrates a methodology 400B for utilizing the fluorophore-labelled analyte specific antibodies to determine whether an analyte is present in a test sample, e.g., in a blood sample. At 440, a test fluid is added to a separation chamber, wherein the separation chamber comprises the first fluid described in FIG. 4A layered with the second fluid described in FIG. 4A, the first liquid is located at a closed end of the chamber. The second fluid comprises the first beads having an analyte attached thereto, the second beads having a metabolite-specific antibody attached thereto, and the plurality of analyte specific antibodies, wherein the first beads have a higher density than a density of the second beads. The second fluid is located closest to an open end of the chamber. The test sample is added to the second fluid. The test sample can be a biological fluid and may further comprise one or more compounds related to a drug, as previously described.

At 450, the chamber and the fluids contained therein (e.g., the first fluid, the second fluid, the test fluid, and their constituents) undergo incubation. During incubation, any of the following can occur: (1) binding between any analyte molecules in the test fluid and the plurality of fluorophore-labelled analyte-specific antibodies in the second fluid, (2) binding between any analyte molecules attached to the first beads and the plurality of fluorophore-labelled analyte-specific antibodies in the second fluid, and/or (3) binding between any metabolites in the test fluid and the metabolite-specific antibodies attached to the second beads in the second fluid.

At 460, a centrifugal force is applied to the chamber causing the first beads with the attached analyte molecules and any respective fluorophore-labelled analyte-specific antibodies attached thereto to pass through the first fluid such that the first beads are displaced to the first layer. The centrifugal force also causing any fluorophore-labelled analyte-specific antibodies with attached analyte molecules to be displaced towards the first fluid, however, owing to the density of the fluorophore-labelled analyte-specific antibodies with attached analyte molecules being less than the density of the first fluid, the fluorophore-labelled analyte-specific antibodies with attached analyte molecules are unable to pass through to the first fluid and the fluorophore-labelled analyte-specific antibodies with attached analyte molecules are constrained in the second fluid. The centrifugal force further causing the second bead with the metabolite-specific antibody and any attached metabolite molecule(s) to be displaced towards the first fluid, however, owing to the density of the second bead being less than the density of the first fluid, the second beads are unable to pass through to the first fluid and the second beads are constrained in the second fluid. In an embodiment, the density of the first beads is higher than the density of the first fluid, and the density of the first fluid is higher than the density of the second beads and the fluorophore-labelled analyte-specific antibodies.

At 470, the first fluid is irradiated with light, wherein the light has a frequency to facilitate fluorescence of any fluorophore-labelled analyte-specific antibodies located in the first fluid, wherein any fluorophore-labelled analyte-specific antibodies located in the first fluid are bound to the analytes attached to the first beads.

At 480, a magnitude of fluorescence is measured at the first fluid, wherein the magnitude of fluorescence is based upon the amount of fluorophore-labelled analyte-specific antibodies located in the first fluid. Based upon the measured magnitude of fluorescence, a volume of analyte, delta-9-THC, present in the first fluid is determined, and further based thereon, an amount of delta-9-THC molecules in the test fluid can be assayed.

At 490, in response to a determination that YES, a degree of fluorescence measured at the first fluid is below a threshold value, a determination can be made that the test fluid contains an amount of analyte that is above a defined limit (e.g., a legal limit). Accordingly, based thereon, a determination can be made that the test fluid was taken from an individual who was in a current state of legally defined intoxication and further determination of the degree of intoxication of the individual should be performed (e.g., back at a police station).

At 495, in response to a determination that NO, a degree of fluorescence measured at the first fluid is below a threshold value, a determination can be made that the test fluid does not contain an amount of analyte that is above a defined limit (e.g., a legal limit). Accordingly, based thereon, a determination can be made that the test fluid was taken from an individual who was not in a current state of legally defined intoxication and the individual can be released from further testing. Method 4B can end at the outcomes of either 490 or 495.

Figure 5:
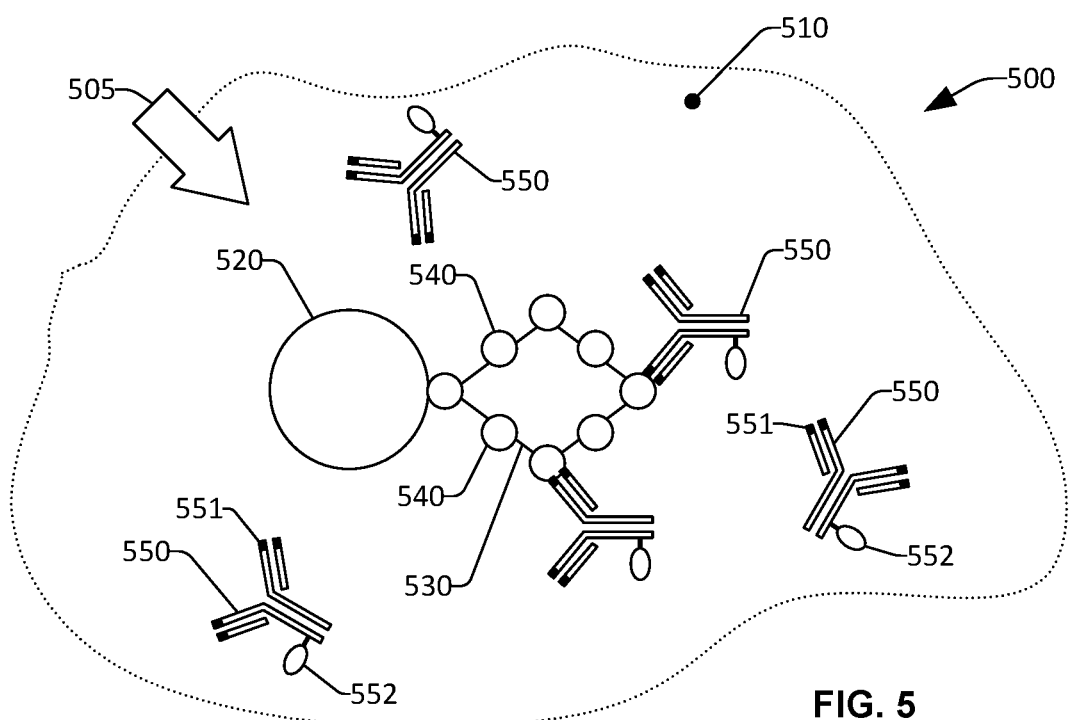
FIG. 5 presents a schematic of a bead with a protein, analyte, and an antibody attached thereto, according to an embodiment.
Figure 6:
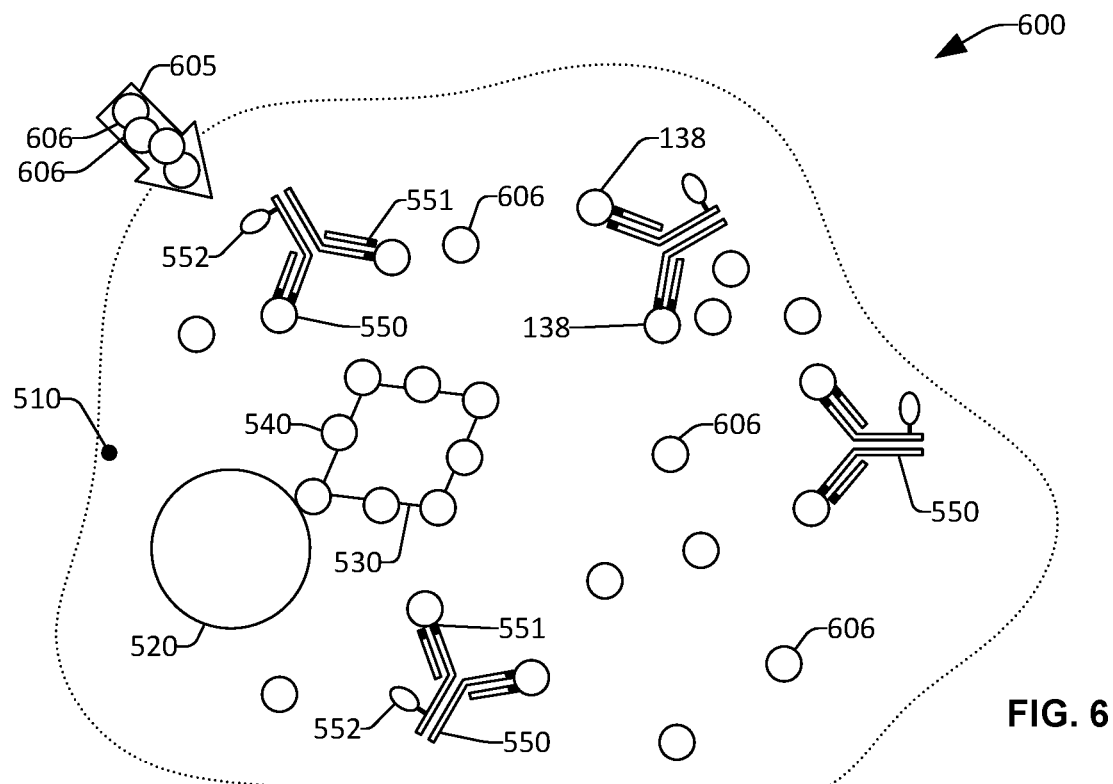
FIG. 6 presents a schematic of a bead with a protein attached thereto, and an analyte attached to an antibody, according to an embodiment.

Turning to FIGS. 5 and 6, schematics 500 and 600 are presented illustrating how a bead with an unlabeled conjugate can be utilized to detect the presence of a drug and/or its metabolites. As previously mentioned with reference to identifying use of marijuana in a situation where the use is legal, but impairment due to the use of the drug is required, a process is required to differentiate the compound (e.g., delta-9-THC) that can cause such impairment from metabolites generated from the compound. Hence, the prior embodiments are directed towards identifying a particular compound in a plurality of compounds that may be existent from use of a drug that is legal in a first jurisdiction and illegal in a second jurisdiction. However, other drugs are still illegal across the United States, and thus, there is only a requirement to detect the presence of a chemical compound relating to the illegal drug to make a determination that an individual has used (e.g., ingested, injected, smoked, etc.) the drug.

FIG. 5, schematic 500 depicts a situation where a sample 505 is taken from an individual who has not used the illegal drug, and hence, there is no chemical in their body that can be linked to the illegal drug. A test fluid 510 includes a bead 520, wherein the bead 520 has a drug conjugate attached thereto. The drug conjugate can be of any form, as required to enable detection of the illegal drug. In an example, the drug conjugate can comprise a protein 530 (e.g., bovine serum albumin (BSA), keyhole limpet hemocyanin (KLH), etc.) and an analyte 540, wherein the analyte 540 is a compound derived from the illegal drug, the presence (or not) of which is to be determined. The test fluid 510 further comprises an antibody 550, wherein the antibody 550 is specific to the analyte 540. To enable detection of location of the antibody 550, as further explained below, the antibody 550 can have a property that enables its detection. For example, when irradiated with light, the antibody 550 can fluoresce (as previously described with reference to antibodies 340), wherein the antibody 550 can include a fluorophore 552 (similar to the fluorophore 342) and analyte specific regions 551 (similar to the specific regions 341).

As shown in schematic 500, owing to the sample 505 being taken from an individual who has not taken the illegal drug, owing to no drug being present in the sample 505, the antibodies 550 bind with the analyte 540 attached to the bead 520 via the protein 530.

FIG. 6, schematic 600 depicts a situation where a sample 605 is taken from an individual who has used the illegal drug, and hence, there is a compound 606 in their body that can be linked to the illegal drug. Addition of the sample 605 to the test fluid 510 results in analyte 606 (a drug compound) being added to the test fluid 610. As previously mentioned, the test fluid 510 includes a bead 520, wherein the bead 520 has a drug conjugate attached thereto, the drug conjugate comprises a protein 530 and the analyte 540, wherein the analyte 540 is a compound derived from the illegal drug, wherein the analytes 606 and 540 can be the same compound, alternatively the analytes 606 and 540 can be differing compounds, but the differing compounds are both related to the illegal drug, the presence (or not) of which is to be determined. The test fluid 510 further comprises the antibody 550 (e.g., a labeled antibody), wherein the antibody 550 is specific to the analyte 540. To enable detection of location of the antibody 550, as further explained below, the antibody 550 can have a property that enables its detection. For example, when irradiated with light, the antibody 550 fluoresces.

As shown in schematic 600, owing to the sample 605 has been taken from an individual who has taken the illegal drug, and owing to the drug being present in the sample 605 (e.g., in the form of analytes 606), the antibodies 550 preferentially bind with the analytes 606, and no (or a minimal number) antibodies 550 bind with the analytes 540 attached to bead 520.

Hence, comparing FIG. 5 with FIG. 6, in a situation where a sample 505 does not contain an illegal drug, or compounds based thereon, per FIG. 5, the antibody 550 is attached to the bead 520 and the drug conjugate attached thereto comprising the protein 530 and the analyte 540. Per FIG. 6, in a situation where a sample 605 does contain an illegal drug, or compounds based thereon, e.g., analyte 606, the antibody 550 is attached to the analyte 606. Consequently, per FIG. 6, the bead 520 and the drug conjugate attached thereto comprising the protein 530 and the analyte 540 do not have an antibody 550 attached thereto. Hence, as further explained below, by separating the bead 520 from the test fluid 510, it is possible to detect the presence of an analyte 540 (per FIG. 5) or not (per FIG. 6) bound to the bead 520, and accordingly, a determination can be made regarding where a sample (e.g., respective samples 505 and 605) contains a drug-related compound, and further, whether an individual from whom the sample was taken, has used the drug.

Figure 7:
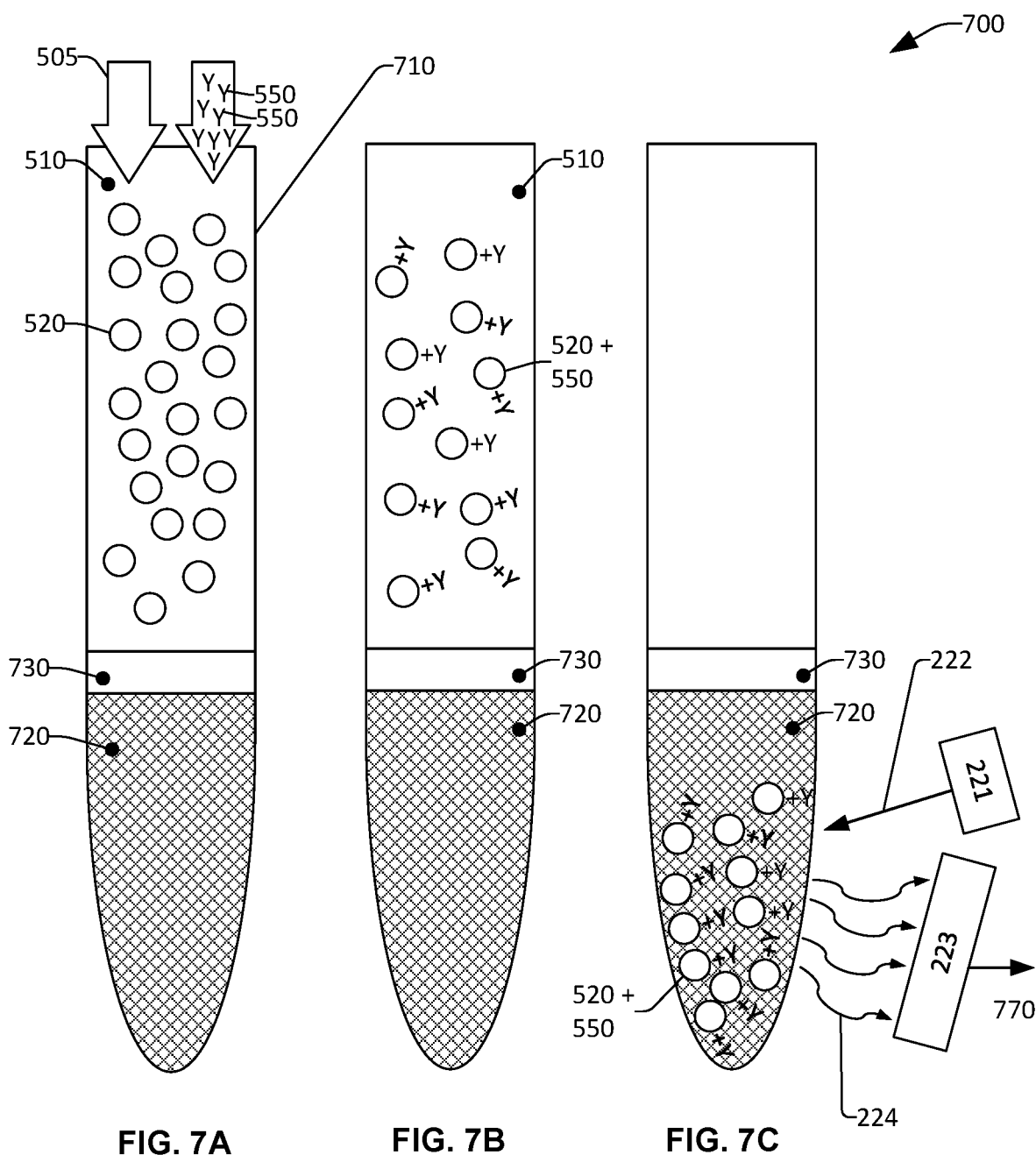
FIG. 7A illustrates an initial test condition where a test sample and an antibody is added to a separation chamber, according to an embodiment.
FIG. 7B illustrates a condition in a separation chamber after an incubation period, according to an embodiment.
FIG. 7C illustrates a condition in a separation chamber after application of a centrifugal force, according to an embodiment.

FIGS. 7A-C, schematic 700 illustrates a separation process comprising density beads being separated from a test fluid. FIGS. 7A-C can be read in conjunction with FIG. 5. As shown in FIG. 7A, a chamber 710 (e.g., a microchannel) comprises a first fluid 720 which is separated from a test fluid 510 by a third fluid 730, wherein the first fluid 720 is located at a closed end of the chamber 710, and the third fluid 730 is an intermediate fluid located between the first fluid 720 and the test fluid 510. The third fluid 730 can function as a density sieve, wherein the third fluid 730 acts to allow the beads 520 pass through to the first fluid region 720, owing to the mass of the beads 520, but prevents lower mass components such as the analyte molecules 550 having the analyte 606 attached thereto to remain in the test fluid 510. As further shown in FIG. 7A, the test fluid 510 comprises a plurality of beads 520, wherein the beads 520 have a drug conjugate attached thereto, the drug conjugate comprises a protein 530 and the analyte 540 (as described in FIG. 5). A sample fluid 505 is added to a test fluid 510, however (as described in FIG. 5), the sample fluid 505 does not contain any analyte. Further, antibodies 550 are added to the test fluid 510 comprising the beads 520.

As shown in FIG. 7B, after an incubation period, the antibodies 550 bind to the beads 520 (e.g., via the analytes 540). It is to be noted that after the incubation period, no beads 520 are located in the fluid 720.

FIG. 7C illustrates conditions in the chamber 710 after a centrifugal force has been applied to the chamber 710 and the various components located therein. Owing to the application of the centrifugal force, the density of the beads 520 has caused them to be moved into the fluid 720. As previously mentioned, the beads 520 can be formed from a material having a density such that upon application of the centrifugal force (e.g., by spinning a disk upon which the chamber 710 is located), the beads 520 (and the attached antibodies 550) pass through the density sieve formed by the layer 730. As previously mentioned, the antibodies 550 can be configured to have a property to enable the location of the antibodies 550 to be determined. In the example presented in FIGS. 7A-7C, when stimulated by an electromagnetic energy (e.g., a light 222) the antibodies 550 will fluoresce. Hence, a light source 221 (e.g., can be located proximate to the portion of the chamber 710 comprising the fluid 720, and a light 222 is directed towards the beads 520 and the attached antibodies 550. Upon stimulation by the light 222, the antibodies 550 fluoresce, with emitted light 224 generated by the fluorescence effect being captured and/or detected by a detector 223. The detector 223 can be configured to generate a signal 770 indicating any of a magnitude of fluorescence measured by the detector 760, whether any fluorescence was measured (e.g., a simple binary signal, 1=fluorescence detected, 0=no fluorescence detected), etc.

Figure 8:
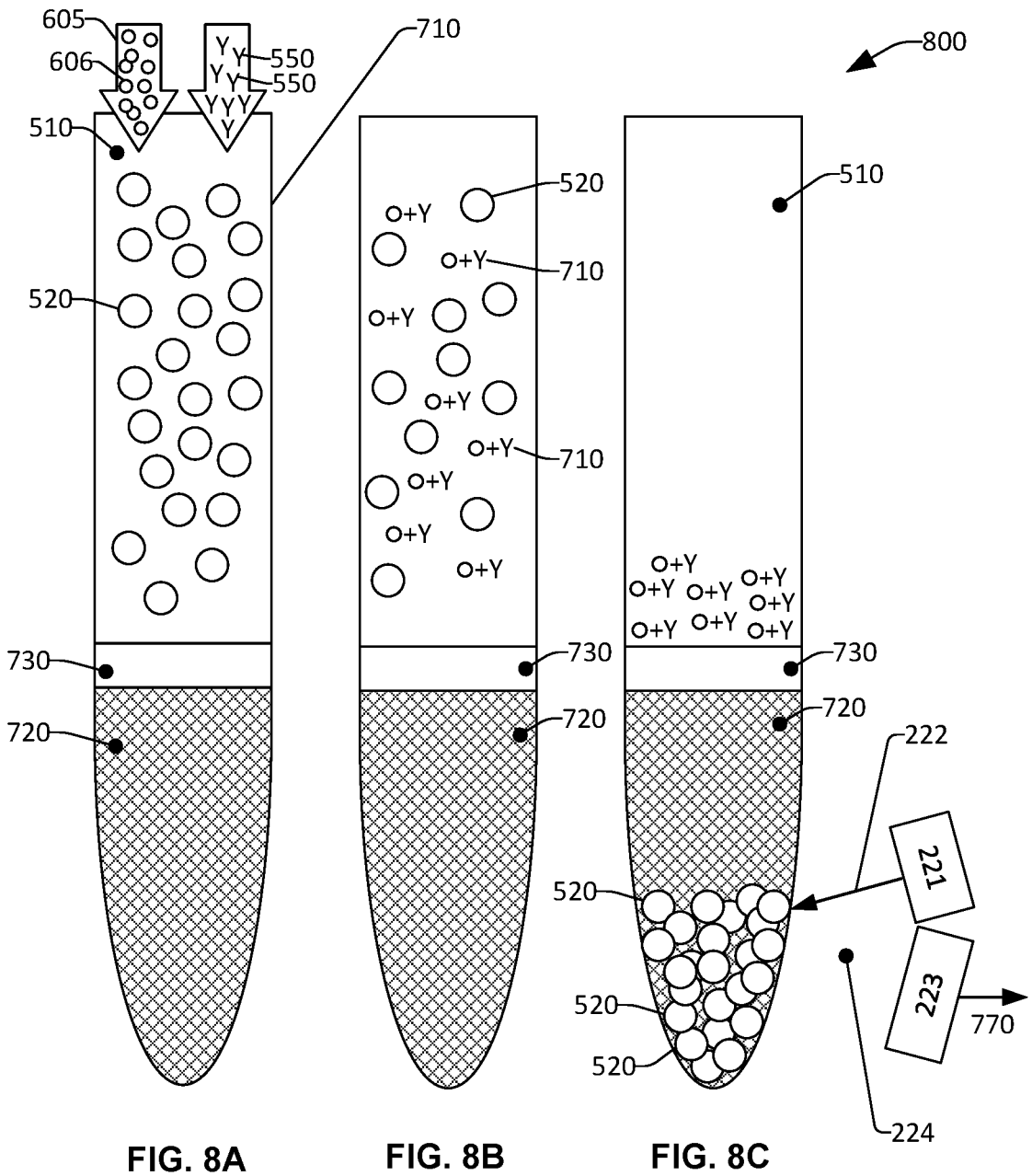
FIG. 8A illustrates an initial test condition where a test sample and an antibody is added to a separation chamber, according to an embodiment.
FIG. 8B illustrates a condition in a separation chamber after an incubation period, according to an embodiment.
FIG. 8C illustrates a condition in a separation chamber after application of a centrifugal force, according to an embodiment.

FIGS. 8A-C, schematic 800 illustrates a separation process comprising density beads being separated from a test fluid, however, in comparison with FIGS. 7A-C, a user has been using the illegal drug in question. FIGS. 8A-C can be read in conjunction with FIG. 6. As shown in FIG. 8A, the chamber 710 comprises the first fluid 720 separated from the test fluid 510 by a third fluid 730, wherein the first fluid 720 is located at a closed end of the chamber 710, and the third fluid 730 is an intermediate fluid located between the first fluid 720 and the test fluid 510. As previously mentioned, the third fluid 730 can function as a density sieve. As further shown in FIG. 8A, the test fluid 510 comprises a plurality of beads 520, wherein the beads 520 have a drug conjugate attached thereto, the drug conjugate comprises a protein 530 and the analyte 540 (as described in FIG. 6).

A sample fluid 605 is added to a test fluid 510, wherein (as described in FIG. 6), the sample fluid 605 contains an analyte(s) 606. Further, antibodies 550 are added to the test fluid 510 comprising the beads 520 and the analyte 606.

As shown in FIG. 8B, after an incubation period, the analytes 606 in the sample 605 bind to the antibodies 550. It is to be noted that after the incubation period, no beads 520 or analytes 606 are located in the fluid 720.

FIG. 8C illustrates conditions in the chamber 710 after a centrifugal force has been applied to the chamber 710 and the various components located therein. Owing to the application of the centrifugal force, the density of the beads 520 has caused them to be moved into the fluid 720. However, the antibodies 550 remain attached to the analytes 606, which, even under the application of the centrifugal force, remain in the portion of the chamber 710 comprising the test fluid 510, as the combination of antibodies 550 and analytes 606 do not have sufficient density pass through the density sieve formed by the layer 730. As previously mentioned, the antibodies 550 can be configured to have a property to enable the location of the antibodies 550 to be determined. In the example presented in FIGS. 8A-8C, when stimulated by an electromagnetic energy (e.g., a light) the antibodies 550 will fluoresce. However, there are no antibodies 550 in the liquid 720, the beads 520 do not have any fluorescing antibodies 550 attached thereto. Hence, when a light source 221 is located proximate to the portion of the chamber 710 comprising the fluid 720, and a light 222 is directed towards the beads 520, no fluorescing occurs in region 810 as there are no antibodies attached to the beads 520. Thus, no light fluorescence is detected at the detector 223. Accordingly, the detector 760 generates a signal 770 indicating no fluorescence was measured by the detector 760, e.g., signal 770 is 0=no fluorescence detected.

Figure 9:
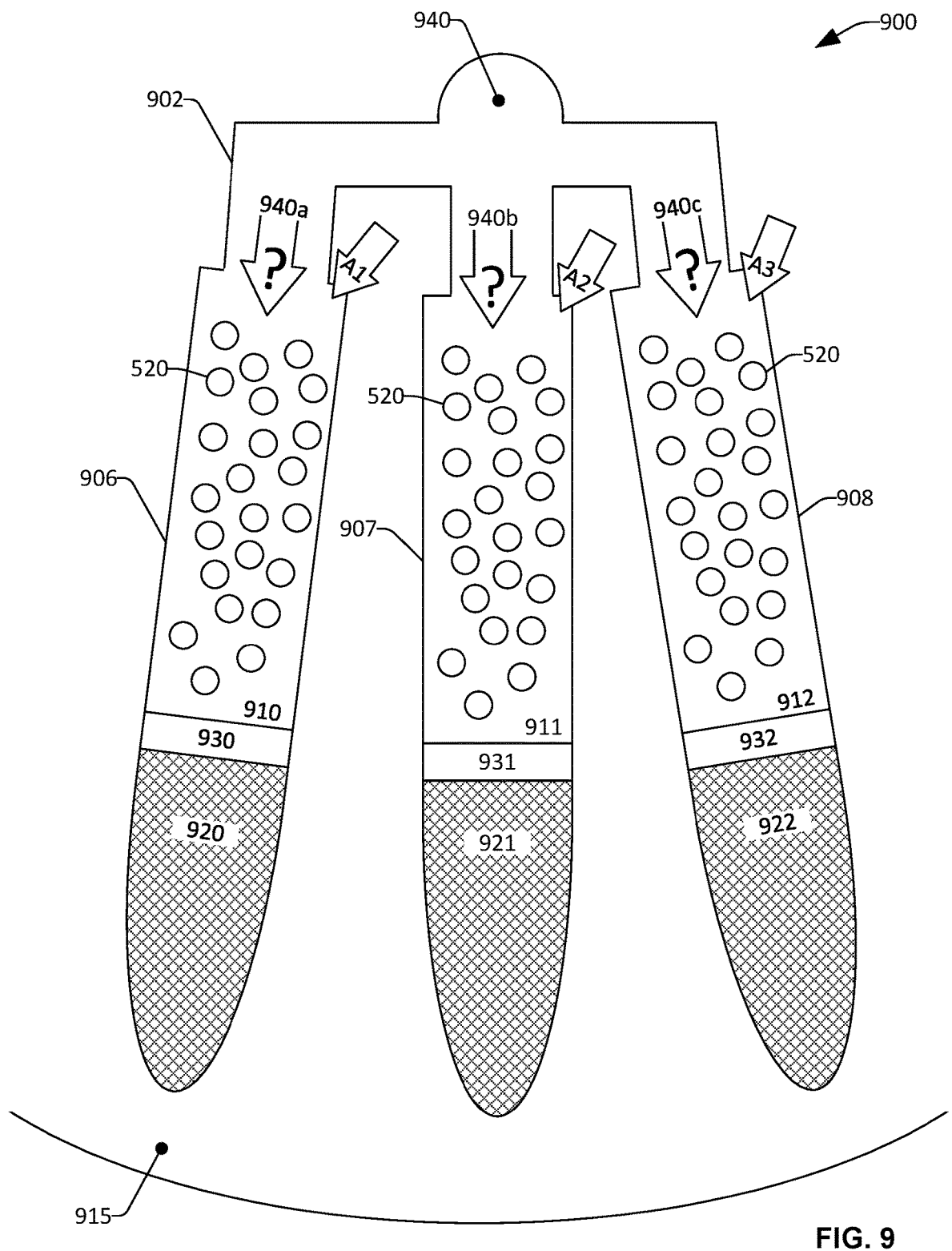
FIG. 9 illustrates concurrent testing for a plurality of compounds, according to an embodiment.

FIG. 9 illustrates a configuration 900 wherein a single sample can be tested for the presence of a plurality of illegal drugs in one operation. An inlet 902 connects to a plurality of chambers 906, 907, and 908 which are located on a rotatable support 915 (e.g., the previously mentioned disk 100). The chambers 906-908 can be operated in a similar manner to the embodiments presented in FIGS. 5, 6, 7A-C and 8A-C. A first respective portion of the chambers 906-908 includes respective first fluids 910, 911, and 912, wherein each of the first fluids 910-912 include a plurality of beads 520 (wherein each bead 520 has a drug conjugate attached thereto, the drug conjugate comprises a protein 530 and the analyte 540, per FIG. 5). Further, each chamber 906-908 includes a second fluid 920, 921, and 922, wherein the second fluids 920-922 are respectively located at a closed end of each respective chamber 906-908. Separating each first fluid from each second fluid in each respective chamber 906-908 is a third fluid, respectively 930, 931, and 932, wherein the third fluids are sieve layers, which as previously described, enable passage of material having a first density through the sieve layer, but prevent passage of a material having a second density through the sieve layer.

A sample 940 (e.g., a blood sample) can be added at the inlet 902, wherein a first portion 940a of the sample 940 enters the first chamber 906, a second portion 940b of the sample 940 enters the second chamber 907, and a third portion 940c of the sample 940 enters the third chamber 908. As indicated by the question mark symbols "?", whether a particular drug is included in the sample 940 is unknown. Further, specific antibodies A1, A2, and A3 can be respectively added to each respective chamber 906, 907 and 908. Each antibody A1-A3 can be directed at a different drug, e.g., A1 can be a cocaine-based antibody, A2 can be a methamphetamine-based antibody, A3 can be a heroin-based antibody, etc. Any suitable antibody can be utilized, e.g., cocaine-based, methamphetamine-based, heroin-based, amphetamine-based, ketamine-base, etc. It is to be appreciated that while only three chambers 906, 907, and 908 are illustrated, any number of chambers can be utilized based, for example, on the number of antibodies that are to be detected. After a period of incubation, as previously described, the disk 915 can be rotated, wherein a centrifugal force applied to the beads 520 causes the beads to move to the respective portions of the chambers 906-908 which includes the respective second fluids 920, 921, and 922. The second fluids 920-922, and the beads 520 respectively included therein, can be analyzed by the emitter 730 and the detector 760. As previously mentioned, in the event of no fluorescence being detected in any of the second fluids 920-922 then a determination can be made that the respective antibody for that fluid has been bound to an analyte present in the sample, and the individual can be considered to have used the drug related to the antibody. Alternatively, as previously described, if any of the second fluids 920-922 and the beads 520 respectively included therein, fluoresce, then the respective antibody A1-A3 can be considered to be bound to the beads 520 and the individual can be deemed to have not used the drug related to the antibody.

It is to be appreciated that while FIGS. 7A-9 utilize a density sieve (e.g., any of layers 730, 930, 931, 932), the density sieve does not have to be present and a two layer configuration similar to that presented in FIGS. 1-3F can be utilized, wherein the liquid nearest the closed end of the chamber has a higher density than the liquid near the opening.

The following presents various assay conditions optimized for whole blood samples, urine, and saliva. As shown the performance is substantially identical across the biological fluid tested. As further shown, the limits of detection are well within established testing parameters stipulated by the United States Department of Transportation (DOT).

TABLE 1

Cocaine in blood assay.

Anti-Benzoylecgonine antibody (BB.868 (US Bio) was chosen for thorough characterization
    Best performance with BSA-drug conjugate on bead
    Fluorescently-labeled antibody in solution
    Optimal results with following parameters:
        Average of 6.2 dye molecules per antibody
        53 nM detector antibody (8 µg/mL); 6% wt/vol beads (60 mg/mL)
        6 µL reaction volumes (4 µL sample, 2 µL detector suspension)
        Loaded 15 µg (±3 µg) of BSA-drug conjugate per 1 mg beads
Limit of detection 8.11 ng/mL in whole blood
Coefficients of variation (tested 20 ng/mL in 20 channels [intra] × 5 discs [inter])
    Intra-assay - 5%
    Inter-assay - 8%

TABLE 2

Methamphetamine in blood assay.

MET2 (LifeSpan) was chosen for thorough characterization
    Best performance with KLH-drug conjugate on bead
    Fluorescently-labeled antibody in solution
    Optimal results with following parameters:
        Average of 3.7 dye molecules per antibody
        45 nM detector antibody (6.75 µg/mL)
        6 µL reaction volumes (4 µL sample, 2 µL detector suspension)
        Loaded 18 µg (±2 µg) of KLH-drug conjugate per 1 mg beads
Limit of detection 11.8 ng/mL in whole blood
Coefficients of variation (tested 35 ng/mL in 20 channels [intra] × 5 discs [inter])
    Intra-assay - 9%
    Inter-assay - 11%

For testing with saliva as the biological fluid, assay performance was substantially equivalent using pooled, normal human saliva for matrix. Wherein cocaine: 7.9 ng/mL LoD, and THC: 550 pg/mL LoD.

For testing with urine as the biological fluid, assay performance was substantially equivalent using pooled, normal human saliva for matrix. Wherein cocaine: 7.7 ng/mL LoD, and THC: 490 pg/mL LoD.

Figure 10:
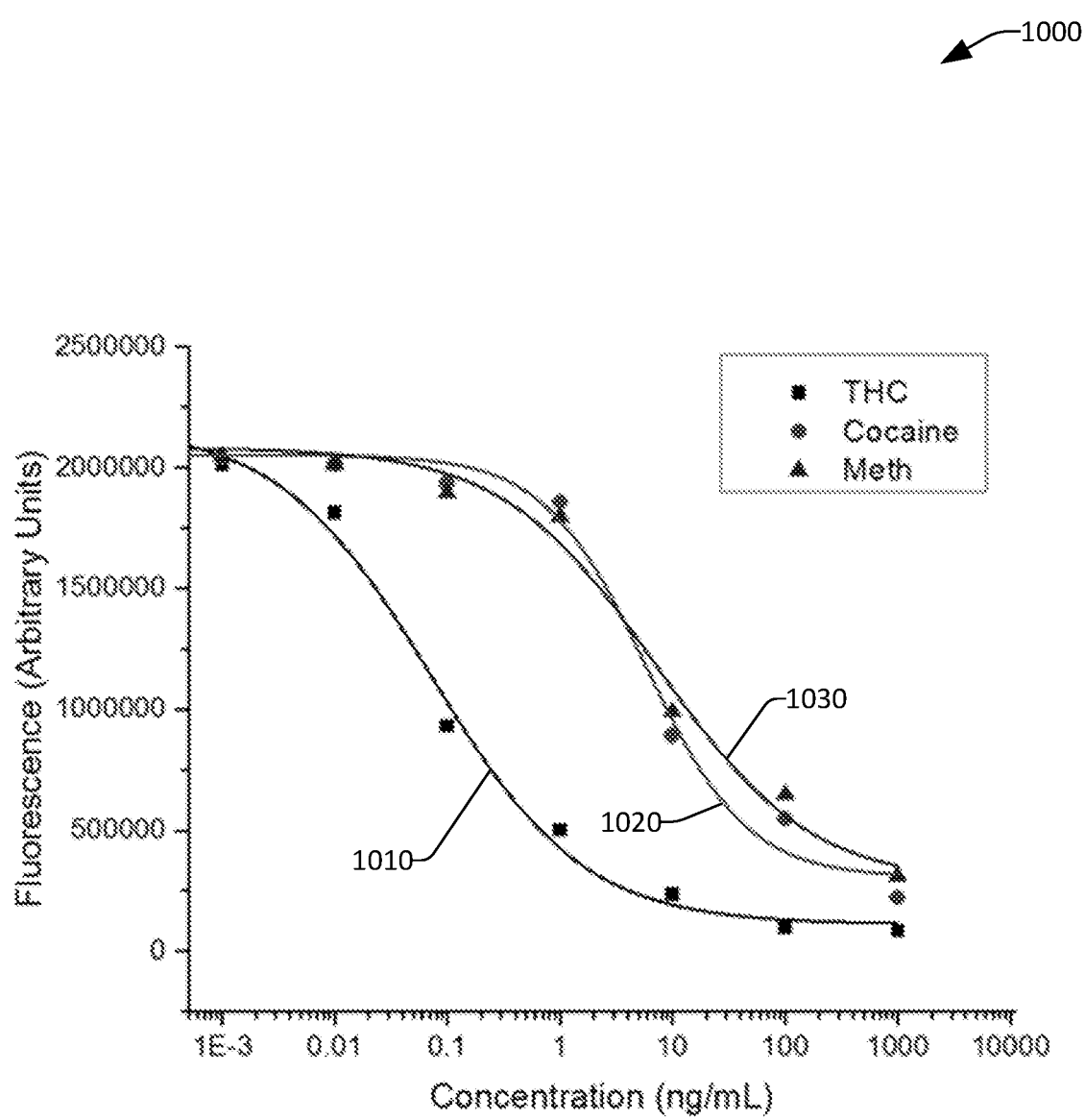
FIG. 10 presents a graph of fluorescence versus concentration for various drugs, according to at least one embodiment.

FIG. 10 presents graph 1000 of fluorescence (arbitrary units) versus concentration (ng/mL) for various drugs, plot 1010 is THC, plot 1020 is cocaine, and plot 1030 is methamphetamine.

Figure 11:
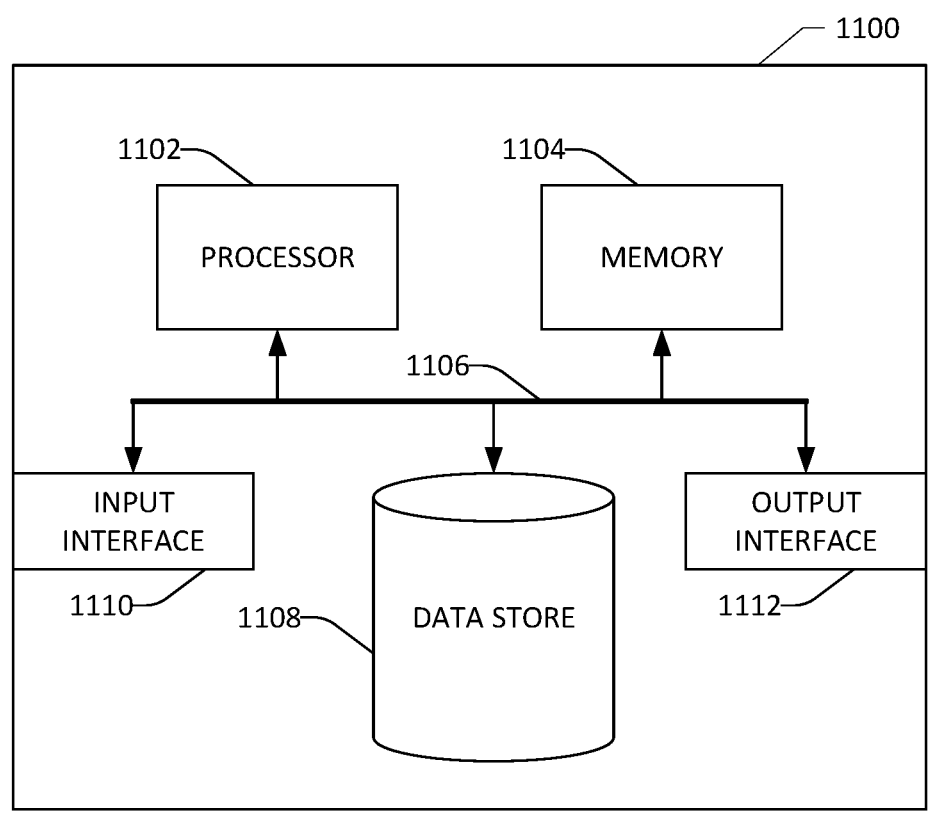
FIG. 11 illustrates an exemplary computing device.

Referring now to FIG. 11, a high-level illustration of an exemplary computing device 1100 that can be used in accordance with the systems and methodologies disclosed herein is illustrated. For instance, the computing device 1100 can be utilized to enable determination of whether a sample taken from an individual includes a compound(s) indicating drug usage. For example, computing device 1100 can operate as the control system 230. The computing device 1100 includes at least one processor 1102 that executes instructions that are stored in a memory 1104. The instructions may be, for instance, instructions for implementing functionality described as being carried out by one or more components discussed above or instructions for implementing one or more of the methods described above. The processor 1102 may access the memory 1104 by way of a system bus 1106. In addition to storing executable instructions, the memory 1104 may also store operating parameters, required operating parameters, and so forth.

The computing device 1100 additionally includes a data store 1108 that is accessible by the processor 1102 by way of the system bus 1106. The data store 1108 may include executable instructions, operating parameters, required operating parameters, etc. The computing device 1100 also includes an input interface 1110 that allows external devices to communicate with the computing device 1100. For instance, the input interface 1110 may be used to receive instructions from an external computer device, from a user, etc. The computing device 1100 also includes an output interface 1112 that interfaces the computing device 1100 with one or more external devices. For example, the computing device 1100 may display text, images, etc., by way of the output interface 1112.

Additionally, while illustrated as a single system, it is to be understood that the computing device 1100 may be a distributed system. Thus, for instance, several devices may be in communication by way of a network connection and may collectively perform tasks described as being performed by the computing device 1100.

Various functions described herein can be implemented in hardware, software, or any combination thereof. If implemented in software, the functions can be stored on or transmitted over as one or more instructions or code on a computer-readable medium. Computer-readable media includes computer-readable storage media. A computer-readable storage media can be any available storage media that can be accessed by a computer. By way of example, and not limitation, such computer-readable storage media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Disk and disc, as used herein, include compact disc (CD), laser disc, optical disc, digital versatile disc (DVD), floppy disk, and Blu-ray disc (BD), where disks usually reproduce data magnetically and discs usually reproduce data optically with lasers. Further, a propagated signal is not included within the scope of computer-readable storage media. Computer-readable media also includes communication media including any medium that facilitates transfer of a computer program from one place to another. A connection, for instance, can be a communication medium. For example, if the software is transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio and microwave are included in the definition of communication medium. Combinations of the above should also be included within the scope of computer-readable media.

What has been described above includes examples of one or more embodiments. It is, of course, not possible to describe every conceivable modification and alteration of the above structures or methodologies for purposes of describing the aforementioned aspects, but one of ordinary skill in the art can recognize that many further modifications and permutations of various aspects are possible. Accordingly, the described aspects are intended to embrace all such alterations, modifications, and variations that fall within the spirit and scope of the appended claims. Furthermore, to the extent that the term "includes" is used in either the details description or the claims, such term is intended to be inclusive in a manner similar to the term "comprising" as "comprising" is interpreted when employed as a transitional word in a claim.

What is claimed is:

1. A method comprising:
providing a chamber that has an open end and a closed end, the chamber comprising a first fluid and a second fluid, wherein the second fluid is located at the closed end of the chamber and the first fluid is located between the second fluid and the open end of the chamber;
adding a test sample to the first fluid, wherein the test sample comprises a free analyte, wherein:
the first fluid comprises:
a bound analyte;
an antibody that is configured to bind with either the free analyte or the bound analyte, wherein the antibody has a stronger binding affinity for the free analyte than for the bound analyte, wherein the antibody additionally has a fluorophore attached thereto; and
a bead having a protein attached thereto, the protein is configured to bind with the bound analyte;
and further wherein the free analyte from the test sample binds with the antibody in the first fluid subsequent to the test sample being added to the first fluid;
applying a centrifugal force to the chamber, wherein the bead transfers from the first fluid to the second fluid upon the centrifugal force being applied to the chamber;
irradiating the second fluid with light energy, wherein the fluorophore, when present in the second fluid, fluoresces upon being irradiated with the light energy; and
quantifying an amount of the free analyte in the second fluid based upon a magnitude of fluorescence at the second fluid, wherein the quantification is based upon a threshold value.

2. The method of claim 1, wherein the free analyte is a delta-9-tetrahydrocannabinol and the bound analyte is a delta-9-tetrahydrocannabinol.

3. The method of claim 1, wherein the second fluid has a higher density than the first fluid.

4. The method of claim 3, wherein the second fluid comprises a colloidal suspension of silicon nanoparticles, dextran, poly(ethylene glycol), glycerol, sorbitol, iodixanol, cesium chloride, or perfluorodecalin.

5. The method of claim 1, wherein the chamber is located on a rotatable disk.

6. The method of claim 5, wherein the centrifugal force results from spinning the disk.

7. The method of claim 1, wherein the first fluid comprises a second bead, wherein the second bead has a metabolite specific antibody attached thereto, the metabolite specific antibody binds with any metabolite present in the first fluid, wherein the metabolite originates from the test sample, and the second bead has a density lower than the bead and a density of the second fluid.

8. The method of claim 1, wherein the threshold value is based upon a minimum amount of delta-9-THC compound to cause intoxication, and in the event of:
determining a magnitude of the indication from a sensor is below the threshold value, indicating that an amount of the free analyte in the test sample exceeds a minimum amount of delta-9-tetrahydrocannabinol to cause intoxication; or
determining a magnitude of the indication from the sensor is above the threshold value, indicating that an amount of the free analyte in the test sample does not exceed a minimum amount of delta-9-tetrahydrocannabinol to cause intoxication.

9. The method of claim 1, wherein the test sample comprises blood, whole blood, serum, saliva, or urine.

10. The method of claim 1, further comprising a third fluid located between the first fluid and the second fluid.

11. The method of claim 1, further comprising:
providing a portion of the test sample to a second chamber comprising a second antibody, wherein the second antibody is configured to bind with a metabolite.

12. The method of claim 11, wherein the metabolite is a cocaine-based compound, a methamphetamine-based compound, a methamphetamine compound, an amphetamine compound, an opiate-based compound, an MDMA-based compound, a ketamine-based compound, a PCP-based compound, a lysergic acid diethylamide-based compound, or a psilocybin-based compound.

13. The method of claim 1, further comprising:
prior to providing the chamber, adding the second fluid to the chamber such that the second fluid fills a first portion of the chamber, wherein the first portion of the chamber is adjacent to the closed end of the chamber, and forms a first layer of fluid in the chamber;
prior to providing the chamber, adding the first fluid to the chamber, wherein the first fluid constrains the second fluid to the first portion of the chamber, and the first fluid forms a second layer of fluid in the chamber, wherein the first fluid comprises the bead, and the fluorophore-labelled analyte specific antibody; and
incubating the test sample in the first chamber.

14. The method of claim 13, wherein the first fluid further comprises a second bead having a metabolite-specific antibody attached thereto, and wherein the bead has a higher density than a density of the second bead.

* * * * *